(12) United States Patent
Lieber et al.

(10) Patent No.: US 9,102,521 B2
(45) Date of Patent: Aug. 11, 2015

(54) NANOSENSORS AND RELATED TECHNOLOGIES

(75) Inventors: Charles M. Lieber, Lexington, MA (US); Ying Fang, Cambridge, MA (US); Fernando Patolsky, Rehovot (IL)

(73) Assignee: President and Fellows of Harvard College, Cambridge, MA (US)

( * ) Notice: Subject to any disclaimer, the term of this patent is extended or adjusted under 35 U.S.C. 154(b) by 1566 days.

(21) Appl. No.: 12/308,207

(22) PCT Filed: Jun. 11, 2007

(86) PCT No.: PCT/US2007/013700
§ 371 (c)(1),
(2), (4) Date: Dec. 16, 2009

(87) PCT Pub. No.: WO2008/051316
PCT Pub. Date: May 2, 2008

(65) Prior Publication Data
US 2010/0087013 A1 Apr. 8, 2010

Related U.S. Application Data

(60) Provisional application No. 60/812,884, filed on Jun. 12, 2006.

(51) Int. Cl.
*B82Y 30/00* (2011.01)
*B82Y 10/00* (2011.01)
(Continued)

(52) U.S. Cl.
CPC .............. *B82Y 10/00* (2013.01); *C12Q 1/6825* (2013.01); *G01N 27/4145* (2013.01); *G01N 27/4146* (2013.01); *C12Q 2600/156* (2013.01); *H01L 51/0049* (2013.01); *H01L 51/0093* (2013.01)

(58) Field of Classification Search
None
See application file for complete search history.

(56) References Cited

U.S. PATENT DOCUMENTS 3,873,359 A 3/1975 Lando
3,873,360 A 3/1975 Lando
(Continued)

FOREIGN PATENT DOCUMENTS

JP 11-11917 4/1998
JP 2000/31462 1/2000
(Continued)

OTHER PUBLICATIONS

Lieber, Electron Devices Meeting, pp. 21.1.1-21.1.4, (2004).*
(Continued)

*Primary Examiner* — Robert T Crow
(74) *Attorney, Agent, or Firm* — Wolf, Greenfield & Sacks, P.C.

(57) ABSTRACT

The present invention generally relates to nanoscale wire devices and methods for use in determining nucleic acids or other analytes suspected to be present in a sample. For example, a nanoscale wire device can be used to detect single base mismatches within a nucleic acid (e.g., by determining association and/or dissociation rates). In one aspect, dynamical information such as a binding constant, an association rate, and/or a dissociation rate, can be determined between an analyte and a binding partner immobilized relative to a nanoscale wire. In some cases, the nanoscale wire includes a first portion comprising a metal-semiconductor compound, and a second portion that does not include a metal-semiconductor compound. The binding partner, in some embodiments, is immobilized relative to at least the second portion of the nanoscale wire, and the size of the second portion of the nanoscale wire may be minimized and/or controlled in some instances.

15 Claims, 13 Drawing Sheets

(51) Int. Cl.
*C12Q 1/68* (2006.01)
*G01N 27/414* (2006.01)
*H01L 51/00* (2006.01)

(56) References Cited

U.S. PATENT DOCUMENTS

| | | | |
|---|---|---|---|
| 3,900,614 A | 8/1975 | Lando |
| 4,673,474 A | 6/1987 | Ogawa |
| 4,939,556 A | 7/1990 | Eguchi et al. |
| 5,023,139 A | 6/1991 | Birnboim et al. |
| 5,089,545 A | 2/1992 | Pol |
| 5,252,835 A | 10/1993 | Lieber et al. |
| 5,274,602 A | 12/1993 | Glenn |
| 5,453,970 A | 9/1995 | Rust et al. |
| 5,475,341 A | 12/1995 | Reed |
| 5,512,131 A | 4/1996 | Kumar et al. |
| 5,524,092 A | 6/1996 | Park |
| 5,537,075 A | 7/1996 | Miyazaki |
| 5,539,214 A | 7/1996 | Lynch et al. |
| 5,581,091 A | 12/1996 | Moskovits et al. |
| 5,589,692 A | 12/1996 | Reed |
| 5,607,876 A | 3/1997 | Biegelsen et al. |
| 5,620,850 A | 4/1997 | Bamdad et al. |
| 5,640,343 A | 6/1997 | Gallagher et al. |
| 5,726,524 A | 3/1998 | Debe |
| 5,739,057 A | 4/1998 | Tiwari et al. |
| 5,747,180 A | 5/1998 | Miller et al. |
| 5,751,156 A | 5/1998 | Muller et al. |
| 5,776,748 A | 7/1998 | Singhvi et al. |
| 5,824,470 A | 10/1998 | Baldeschwieler et al. |
| 5,830,538 A | 11/1998 | Gates et al. |
| 5,840,435 A | 11/1998 | Lieber et al. |
| 5,847,565 A | 12/1998 | Narayanan |
| 5,858,862 A | 1/1999 | Westwater et al. |
| 5,864,823 A | 1/1999 | Levitan |
| 5,866,434 A | 2/1999 | Massey et al. |
| 5,882,779 A | 3/1999 | Lawandy |
| 5,897,945 A | 4/1999 | Lieber et al. |
| 5,900,160 A | 5/1999 | Whitesides et al. |
| 5,903,010 A | 5/1999 | Flory et al. |
| 5,908,692 A | 6/1999 | Hamers et al. |
| 5,916,642 A | 6/1999 | Chang |
| 5,942,443 A | 8/1999 | Parce et al. |
| 5,985,173 A | 11/1999 | Gray et al. |
| 5,997,832 A | 12/1999 | Lieber et al. |
| 6,004,444 A | 12/1999 | Aksay et al. |
| 6,036,774 A | 3/2000 | Lieber et al. |
| 6,038,060 A | 3/2000 | Crowley |
| 6,060,121 A | 5/2000 | Hidber et al. |
| 6,060,724 A | 5/2000 | Flory et al. |
| 6,069,380 A | 5/2000 | Chou et al. |
| 6,123,819 A | 9/2000 | Peeters |
| 6,128,214 A | 10/2000 | Kuekes et al. |
| 6,143,184 A | 11/2000 | Martin et al. |
| 6,149,819 A | 11/2000 | Martin et al. |
| 6,159,742 A | 12/2000 | Lieber et al. |
| 6,180,239 B1 | 1/2001 | Whitesides et al. |
| 6,187,165 B1 | 2/2001 | Chien et al. |
| 6,190,634 B1 | 2/2001 | Lieber et al. |
| 6,203,864 B1 | 3/2001 | Zhang et al. |
| 6,207,392 B1 | 3/2001 | Weiss et al. |
| 6,211,464 B1 | 4/2001 | Mochizuki et al. |
| 6,231,744 B1 | 5/2001 | Ying et al. |
| 6,248,674 B1 | 6/2001 | Kamins et al. |
| 6,256,767 B1 | 7/2001 | Kuekes et al. |
| 6,270,074 B1 | 8/2001 | Rasmussen et al. |
| 6,278,231 B1 | 8/2001 | Iwasaki et al. |
| 6,286,226 B1 | 9/2001 | Jin |
| 6,287,765 B1 | 9/2001 | Cubicciotti |
| 6,314,019 B1 | 11/2001 | Kuekes et al. |
| 6,325,904 B1 | 12/2001 | Peeters |
| 6,340,822 B1 | 1/2002 | Brown et al. |
| 6,346,189 B1 | 2/2002 | Dai et al. |
| 6,355,198 B1 | 3/2002 | Kim et al. |
| 6,359,288 B1 | 3/2002 | Ying et al. |
| 6,413,802 B1 | 7/2002 | Hu et al. |
| 6,437,329 B1 | 8/2002 | Yedur et al. |
| 6,440,637 B1 | 8/2002 | Choi et al. |
| 6,451,113 B1 | 9/2002 | Givargizov |
| 6,459,095 B1 | 10/2002 | Heath et al. |
| 6,465,132 B1 | 10/2002 | Jin |
| 6,465,331 B1 | 10/2002 | Keeth et al. |
| 6,468,657 B1 | 10/2002 | Hou et al. |
| 6,468,677 B1 | 10/2002 | Benton et al. |
| 6,503,375 B1 | 1/2003 | Maydan et al. |
| 6,528,020 B1 | 3/2003 | Dai et al. |
| 6,538,367 B1 | 3/2003 | Choi et al. |
| 6,559,468 B1 | 5/2003 | Kuekes et al. |
| 6,586,095 B2 | 7/2003 | Wang et al. |
| 6,628,053 B1 | 9/2003 | Den et al. |
| 6,716,409 B2 | 4/2004 | Hafner et al. |
| 6,741,019 B1 | 5/2004 | Filas et al. |
| 6,743,408 B2 | 6/2004 | Lieber et al. |
| 6,756,025 B2 | 6/2004 | Colbert et al. |
| 6,756,795 B2 | 6/2004 | Hunt et al. |
| 6,762,056 B1 | 7/2004 | Peeters |
| 6,781,166 B2 | 8/2004 | Lieber et al. |
| 6,803,840 B2 | 10/2004 | Hunt et al. |
| 6,808,746 B1 | 10/2004 | Dai et al. |
| 6,815,706 B2 | 11/2004 | Li et al. |
| 6,822,051 B2 | 11/2004 | Harris |
| 6,846,565 B2 | 1/2005 | Korgel et al. |
| 6,846,654 B1 | 1/2005 | Blackburn et al. |
| 6,872,645 B2 | 3/2005 | Duan et al. |
| 6,882,767 B2 | 4/2005 | Yang et al. |
| 6,900,479 B2 | 5/2005 | Lieber et al. |
| 6,902,720 B2 | 6/2005 | McGimpsey |
| 6,946,197 B2 | 9/2005 | Yadav et al. |
| 6,958,216 B2 | 10/2005 | Kelley et al. |
| 6,962,823 B2 | 11/2005 | Empedocles et al. |
| 6,963,077 B2 | 11/2005 | Lieber et al. |
| 6,974,706 B1 | 12/2005 | Melker et al. |
| 6,996,147 B2 | 2/2006 | Majumdar et al. |
| 7,048,903 B2 | 5/2006 | Colbert et al. |
| 7,073,157 B2 | 7/2006 | Lieber et al. |
| 7,129,554 B2 | 10/2006 | Lieber et al. |
| 7,172,953 B2 | 2/2007 | Lieber et al. |
| 7,211,464 B2 | 5/2007 | Lieber et |
| 7,254,151 B2 | 8/2007 | Lieber et al. |
| 7,256,466 B2 | 8/2007 | Lieber et al. |
| 7,274,208 B2 | 9/2007 | Lieber et al. |
| 7,301,199 B2 | 11/2007 | Lieber et al. |
| 7,303,875 B1 | 12/2007 | Bock et al. |
| 7,335,908 B2 | 2/2008 | Samuelson et al. |
| 7,351,313 B2 | 4/2008 | Hasegawa et al. |
| 7,385,267 B2 | 6/2008 | Lieber et al. |
| 7,399,691 B2 | 7/2008 | Lieber et al. |
| 7,476,596 B2 | 1/2009 | Lieber et al. |
| 7,500,213 B2 | 3/2009 | Lieber et al. |
| 7,595,260 B2 | 9/2009 | Lieber et al. |
| 7,619,290 B2 | 11/2009 | Lieber et al. |
| 7,659,165 B2 | 2/2010 | Koenenkamp |
| 2001/0054709 A1 | 12/2001 | Heath et al. |
| 2002/0013031 A1 | 1/2002 | Chen et al. |
| 2002/0040805 A1 | 4/2002 | Swager |
| 2002/0055239 A1 | 5/2002 | Tuominen et al. |
| 2002/0084502 A1 | 7/2002 | Jang et al. |
| 2002/0086335 A1 | 7/2002 | Massey et al. |
| 2002/0112814 A1 | 8/2002 | Hafner et al. |
| 2002/0117659 A1 | 8/2002 | Lieber et al. |
| 2002/0122766 A1 | 9/2002 | Lieber et al. |
| 2002/0130311 A1 | 9/2002 | Lieber et al. |
| 2002/0130353 A1 | 9/2002 | Lieber et al. |
| 2002/0146714 A1 | 10/2002 | Lieber et al. |
| 2002/0146745 A1 * | 10/2002 | Natan et al. .................. 435/7.1 |
| 2002/0158342 A1 | 10/2002 | Tuominen et al. |
| 2002/0172820 A1 | 11/2002 | Majumdar et al. |
| 2002/0175408 A1 | 11/2002 | Majumdar et al. |
| 2002/0179434 A1 | 12/2002 | Dai et al. |
| 2002/0187504 A1 | 12/2002 | Reich et al. |
| 2003/0001091 A1 | 1/2003 | Nakayama et al. |
| 2003/0003300 A1 | 1/2003 | Korgel et al. |
| 2003/0032892 A1 | 2/2003 | Erlach et al. |
| 2003/0048619 A1 | 3/2003 | Kaler et al. |

(56) References Cited

U.S. PATENT DOCUMENTS

| | | |
|---|---|---|
| 2003/0073071 A1 | 4/2003 | Fritz et al. |
| 2003/0089899 A1 | 5/2003 | Lieber et al. |
| 2003/0098488 A1 | 5/2003 | O'Keeffe et al. |
| 2003/0113713 A1 | 6/2003 | Glezer et al. |
| 2003/0113940 A1 | 6/2003 | Erlanger et al. |
| 2003/0121764 A1 | 7/2003 | Yang et al. |
| 2003/0124509 A1 | 7/2003 | Kenis et al. |
| 2003/0124717 A1 | 7/2003 | Awano et al. |
| 2003/0134267 A1 | 7/2003 | Kang et al. |
| 2003/0134433 A1 | 7/2003 | Gabriel et al. |
| 2003/0135971 A1 | 7/2003 | Liberman et al. |
| 2003/0156992 A1 | 8/2003 | Anderson et al. |
| 2003/0186522 A1 | 10/2003 | Duan et al. |
| 2003/0186544 A1 | 10/2003 | Matsui et al. |
| 2003/0189202 A1 | 10/2003 | Li et al. |
| 2003/0197456 A1 | 10/2003 | Den et al. |
| 2003/0200521 A1 | 10/2003 | DeHon et al. |
| 2004/0005723 A1 | 1/2004 | Empedocles et al. |
| 2004/0026684 A1 | 2/2004 | Empedocles |
| 2004/0067530 A1 | 4/2004 | Gruner |
| 2004/0095658 A1 | 5/2004 | Buretea et al. |
| 2004/0106203 A1 | 6/2004 | Stasiak et al. |
| 2004/0112964 A1 | 6/2004 | Empedocles et al. |
| 2004/0113138 A1 | 6/2004 | DeHon et al. |
| 2004/0113139 A1 | 6/2004 | DeHon et al. |
| 2004/0118448 A1 | 6/2004 | Scher et al. |
| 2004/0133118 A1 | 7/2004 | Llinas |
| 2004/0136866 A1 | 7/2004 | Pontis et al. |
| 2004/0146560 A1 | 7/2004 | Whiteford et al. |
| 2004/0157414 A1 | 8/2004 | Gole et al. |
| 2004/0188721 A1 | 9/2004 | Lieber et al. |
| 2004/0191517 A1 | 9/2004 | Drake |
| 2004/0213307 A1 | 10/2004 | Lieber et al. |
| 2005/0037374 A1 | 2/2005 | Melker et al. |
| 2005/0064185 A1 | 3/2005 | Buretea et al. |
| 2005/0064731 A1 | 3/2005 | Park et al. |
| 2005/0066883 A1 | 3/2005 | Dubrow et al. |
| 2005/0072213 A1 | 4/2005 | Besnard et al. |
| 2005/0079533 A1 | 4/2005 | Samuelson et al. |
| 2005/0079659 A1 | 4/2005 | Duan et al. |
| 2005/0100960 A1 | 5/2005 | Dai et al. |
| 2005/0101026 A1 | 5/2005 | Sailor et al. |
| 2005/0106713 A1 | 5/2005 | Phan et al. |
| 2005/0109989 A1 | 5/2005 | Whiteford et al. |
| 2005/0110064 A1 | 5/2005 | Duan et al. |
| 2005/0117441 A1 | 6/2005 | Lieber et al. |
| 2005/0133254 A1 | 6/2005 | Tsakalakos |
| 2005/0161662 A1 | 7/2005 | Majumdar et al. |
| 2005/0181587 A1 | 8/2005 | Duan et al. |
| 2005/0201149 A1 | 9/2005 | Duan et al. |
| 2005/0202615 A1 | 9/2005 | Duan et al. |
| 2005/0212079 A1 | 9/2005 | Stumbo et al. |
| 2005/0214967 A1 | 9/2005 | Scher et al. |
| 2005/0219788 A1 | 10/2005 | Chow et al. |
| 2005/0224778 A1 | 10/2005 | Dubin et al. |
| 2005/0230356 A1 | 10/2005 | Empedocles et al. |
| 2005/0253137 A1 | 11/2005 | Whang et al. |
| 2005/0257821 A1 | 11/2005 | Ramanathan et al. |
| 2005/0266662 A1 | 12/2005 | Yi |
| 2005/0275010 A1 | 12/2005 | Chen et al. |
| 2005/0287717 A1 | 12/2005 | Heald et al. |
| 2006/0008942 A1 | 1/2006 | Romano et al. |
| 2006/0009003 A1 | 1/2006 | Romano et al. |
| 2006/0019472 A1 | 1/2006 | Pan et al. |
| 2006/0054936 A1 | 3/2006 | Lieber et al. |
| 2006/0057360 A1 | 3/2006 | Samuelson et al. |
| 2006/0160246 A1 | 7/2006 | Massey et al. |
| 2006/0175601 A1 | 8/2006 | Lieber et al. |
| 2006/0237749 A1 | 10/2006 | Lieber et al. |
| 2006/0269927 A1 | 11/2006 | Lieber et al. |
| 2007/0026645 A1 | 2/2007 | Lieber et al. |
| 2007/0032023 A1 | 2/2007 | Lieber et al. |
| 2007/0032051 A1 | 2/2007 | Lieber et al. |
| 2007/0032052 A1 | 2/2007 | Lieber et al. |
| 2007/0048492 A1 | 3/2007 | Lieber et al. |
| 2007/0158766 A1 | 7/2007 | Lieber et al. |
| 2007/0252136 A1 | 11/2007 | Lieber et al. |
| 2007/0281156 A1 | 12/2007 | Lieber et al. |
| 2008/0161876 A1 | 7/2008 | Wirbisky et al. |
| 2008/0191196 A1 | 8/2008 | Lu et al. |
| 2008/0211040 A1 | 9/2008 | Lieber et al. |
| 2008/0254291 A1 | 10/2008 | Dehon et al. |
| 2009/0004852 A1 | 1/2009 | Lieber et al. |
| 2009/0057650 A1 | 3/2009 | Lieber et al. |
| 2009/0299213 A1 | 12/2009 | Patolsky et al. |
| 2010/0227382 A1 | 9/2010 | Lieber et al. |
| 2014/0080139 A1 | 3/2014 | Lieber et al. |
| 2014/0184196 A1 | 7/2014 | Lieber et al. |

FOREIGN PATENT DOCUMENTS

| | | |
|---|---|---|
| WO | WO 91/06036 A1 | 5/1991 |
| WO | WO 95/02709 A2 | 1/1995 |
| WO | WO 96/29629 A2 | 9/1996 |
| WO | WO 97/33737 A1 | 9/1997 |
| WO | WO 97/34025 A1 | 9/1997 |
| WO | WO 98/39250 A1 | 9/1998 |
| WO | WO 98/48456 A1 | 10/1998 |
| WO | WO 98/42620 A1 | 10/1999 |
| WO | WO 99/63347 A2 | 12/1999 |
| WO | WO 00/09443 A1 | 2/2000 |
| WO | WO 00/17101 A1 | 3/2000 |
| WO | WO 00/19494 A1 | 4/2000 |
| WO | WO 00/51186 A1 | 8/2000 |
| WO | WO 01/03208 A1 | 1/2001 |
| WO | WO 01/44796 A1 | 6/2001 |
| WO | WO 02/17362 A2 | 2/2002 |
| WO | WO 02/31183 A1 | 4/2002 |
| WO | WO 02/48701 A2 | 6/2002 |
| WO | WO 02/086480 A1 | 10/2002 |
| WO | WO 03/005450 A2 | 1/2003 |
| WO | WO 03/016901 A1 | 2/2003 |
| WO | WO 03/053851 A2 | 7/2003 |
| WO | WO 03/054931 A1 | 7/2003 |
| WO | WO 03/063208 A2 | 7/2003 |
| WO | WO 2004/003535 | 1/2004 |
| WO | WO 2004/010552 A1 | 1/2004 |
| WO | WO 2004/032190 A2 | 4/2004 |
| WO | WO 2004/032193 A2 | 4/2004 |
| WO | WO 2004/034025 A2 | 4/2004 |
| WO | WO 2004/109282 A1 | 12/2004 |
| WO | WO 2005/059506 A2 | 6/2005 |
| WO | WO 2005/089165 | 9/2005 |
| WO | WO 2005/093831 A1 | 10/2005 |
| WO | WO 2005/094440 | 10/2005 |
| WO | WO 2005/114282 A1 | 12/2005 |
| WO | WO 2006/107312 A1 | 10/2006 |
| WO | WO 2006/132659 A2 | 12/2006 |
| WO | WO 2008/027078 A2 | 3/2008 |
| WO | WO 2014/031709 A1 | 2/2014 |
| WO | WO 2014/043341 A1 | 3/2014 |

OTHER PUBLICATIONS

Agarwal, R., et al., "Lasing in Single Cadmium Sulfide Nanowire Optical Cavities," *Nano Letters*, vol. 5, No. 5, pp. 917-920 (2005).

Chen et al., "Large on-off ratios and negative differential resistance in a molecular electronic device", *Science*, Nov. 19, 1999, 286:1550-51.

Chen, R.J., et al., "Noncovalent functionalization of carbon nanotubes for highly specific electronic biosensors," *PNAS*, vol. 100, No. 9, pp. 4984-4989 (2003).

Cheung et al., "Diameter Controlled Synthesis of Carbon Nanotubes," *J. Phys. Chem B*, 2002, 106:2429-2433.

Choi, K.J., et al., "Enhancement of Ferroelectricity in Strained BaTiO Thin Films," *Science*, vol. 306, pp. 1005-1009 (2004).

Chung et al., "Silico nanowire devices," *App. Phys. Letters*, 2000, 76(15):2069-2070.

Collier et al., "Electronically configurable molecular-based logic gates," *Science*, 1999, 285:391-394.

Cui et al., "Diameter-controlled synthesis of single-crystal silicon nanowires," *Appl. Phys. Letters*, 2001, 78(15): 2214-2216.

Cui et al., "Doping and Electrical Transport in Silicon Nanowires," *J. Phys. Chem.*, 2000, 104(22):5214-5216.

(56) References Cited

OTHER PUBLICATIONS

Cui et al., "Functional nanoscale electronic devices assembled using silicon nanowire building blocks", *Science*, Feb. 2, 2001, 291:851-853.
Cui et al., "Nanowire nanosensors for highly sensitive and selective detection of biological and chemical species", *Science*, Aug. 17, 2001, 293:1289-1292.
Duan et al., "General Synthesis of Compound Semiconductor Nanowires," *Adv. Mat.*, 2000, 12(4):298-302.
Duan et al., High-performance thin-film transistors using semiconductor nanowires and.
nanoribbons, *Nature*, 2003, 425:274-278.
Duan et al., "Laser-Assisted Catalytic Growth of Single Crystal GaN Nanowires," *J.Am.Chem.Soc.*, 2000, 122:188-189.
Duan et al., "Nonvolatile Memory and Programmable Logic from Molecule-Gated Nanowires," *Nano Letters*, 2002, 2(5):487-490.
Duan et al.., "Indium phosphide nanowires as building blocks for nanoscale electronic and optoelectronic devices," *Nature*, Jan. 4, 2001, 409:66-69.
Duan, X., et al., "Single-nanowire elecrtrically driven lasers," *Nature*, vol. 421, pp. 241-245(2003).
Duan, X., et al., "Synthesis and optical properties of gallium arsenide nanowires," *Applied Physics Letters*, vol. 76, No. 9, pp. 1116-1118 (2000).
Esfarjani et al., "Electronic and transport properties of N-P. doped nanotubes," *Applied Physics Letters*, 1999, 74:79-81.
Friedman, R.S., et al., "High-speed integrated nanowire circuits," *Nature*, vol. 434, pp. 1085 (2005).
Givargizov, "Fundamental aspects of VSL growth", *Journal of Crystal Growth*, 1975, 31:20-30.
Gradecak, S., et al., "GaN nanowire lasers with low lasing thresholds," *Applied Physics Letters*, vol. 87, pp. 173111 (2005).
Gudiksen et al., "Diameter-Selective Synthesis of Semiconductor Nanowires," *J.Am.Chem.Soc.*, 2000, 122, 8801-8802.
Gudiksen et al., "Growth of nanowire superlattice structures for nanoscale photonics and electronics", *Nature*, 2002, 415:617-620.
Gudiksen et al., "Size-Dependent Photoluminescence from Single Indium Phosphide Nanowires," *J. Phys. Chem.*, 2002, 106:4036-4039.
Gudiksen et al., "Synthetic Control of the Diameter and Length of Single Crystal Semiconductor Nanowires," *J. Phys. Chem.*, 2001, 105:4062-4064.
Guo et al., "A Silicon Single-Electron Transistor Memory Operating at Room Temperature," *Science*, 275:649-651, 1997.
Guo et al., "Nanoscale silicon field effect transistors fabricated using implant lithography," *Appl. Phys. Lett.*, 71(13):1881-1883, 1997.
Hahm, J., et al., "Direct Ultrasensitive Electrical Detection of DNA and DNA Sequence Variations Using Nanowire Nanosensors," *Nano Letters*, vol. 4, No. 1, pp. 51-54 (2004).
Haraguchi et al., "GaAs p-n. junction formed in quantum wire crystals," *App. Phys. Letters*, 1992, 60(6):745-747.
Haraguchi et al., "Polarization dependence of light emitted from GaAs p-n. junctions in quantum wire crystals", *Journal of Applied Physics*, Apr. 1994, 75(8): 4220-4225.
Heath, J. R., et al., "A liquid solution synthesis of single crystal germanium quantum wires," *Chemical Physics Letters*, vol. 208, No. 3, 4, pp. 263-268 (1993).
Hiruma, et al., "GaAs fr e-standing quantum-siz wires," *J. Appl. Phys.*, vol. 74, No. 5, pp. 3162 (1993).
Hiruma et al., "Self-organized growth of GaAs/InAs heterostructure nanocylinders by organometallic vapor phase epitaxy", *Journal of Crystal Growth*, 1996, 163: 226-231.
Holmes et al., "Control of Thickness and Orientation of Solution-Grown Silicon Nanowires," *Science*, 2000, 287:1471-1473.
Hu et al., "Chemistry and Physics in One Dimension: Synthesis and Properties of Nanowires and Nanotubes," *Acc. Chem. Res.*, 1999, 32(5):435-445.
Hu et al., "Controlled growth and electrical properties of heterojunctions of carbon nanotubes and silicon nanowires," *Nature*, 1999, 399:48-51.
Hu et al., "Serpentine Superlattice Nanowire-Array Lasers," *IEEE J. Quantum Elec.*, 1995, 31(8):1380-1388.
Huang et al., "Directed assembly of one-dimensional nanostructures into functional networks", *Science*, Jan. 26, 2001, 291: 630-633.
Huang et al., "Gallium Nitride Nanowire Nanodevices," *Nano Letters*, 2002, 2(2):101-104.
Huang et al., "Logic Gates and Computation from Assembled Nanowire Building Blocks," *Science*, 2001, 294:1313-1317.
Huang et al., "Room-Temperature Ultraviolet Nanowire Nanolasers," *Science*, 2001, 292:897-1898.
IBM News, "IBM creates highest performing nanotube transistors" http://www.ibm.com/news/us/2002/05/20.html.
Javey, A., et al., "Ballistic carbon nanotube field-effect transistors," *Nature*, vol. 424, pp. 654 (2003).
Jin et al., "Scalable Interconnection and Integration of Nanowire Devices without Registration," *NanoLetters*, 2004, 4(5):915-919.
Johnson et al., "Single gallium nitride nanowire lasers," *Nature*, 2002, 1: 106-110.
Johnson et al., "Single Nanowire Lasers," *J. Phys. Chem.*, 2001, 105(46):11387-11390.
Joselevich et al., "Vectorial Growth of Metallic and Semiconducting Single-Wall Carbon Nanotubes," *Nano Letters*, 2002, 2(10):1137-1141.
Kanjanachuchai et al., "Coulomb blockade in strained-Si nanowires on leaky virtual substrates", *Semiconductor Science and Technology*, 2001, 16:72-76.
Kong et al., "Chemical vapor deposition of methane for single-walled carbon nanotubes," *Chem. Physics Letters*, 1998, 292:567-574.
Kong et al., "Nanotube molecular wires as chemical sensors", *Science*, Jan. 28, 2000, 287:622-625.
Kong et al., "Synthesis of individual single-walled carbon nanotubes on patterned silicon wafers," *Nature*, 1998, 395:878-881.
Lahoun et al., "Epitaxial core-shell and core-multishell nanowire heterostructures", *Nature*, 2002, 420: 57-61.
Lahoun et al., "Semiconductor nanowire heterostructures," *Phil. Trans. R. Soc. Lond. A*, 2004, 362:1247-1260.
Law, M., et al., "Nanoribbon Waveguides for Subwavelength Photonics Integration," *Science*, vol. 305, pp. 1269-1274 (2004).
Leff, D.V., et al., "Thermodynamic Control of Gold Nanocrystal Size: Experiment and Theory," *J. Phys. Chem.*, vol. 99, pp. 7036-7041 (1995).
Lei, B., et al., "Nanowire transistors with ferroelectric gate dielectrics: Enhanced performance and memory effects," *Applied Physics Letters*, vol. 84, No. 22, pp. 4553-4555 (2004).
Lieber, "Nanoscale Science and Technology: Building a Big Future from Small Things," *MRS Bulletin*, 2003, 486-491.
Lieber, C., "Nanowire Superlattices," *Nano Letters*, vol. 2, No. 2, pp. 81-82 (2002).
Lu, W., et al., "One dimensional hole gas in germanium/silicon nanowire heterostructures," *PNAS*, vol. 102, No. 29, pp. 10046-10051 (2005).
Martel, et al., "Single- and multi-wall carbon nanotube field-effect transistors," *Apl. Phys. Lett.*, 1998, 73(17):2447-2449.
McAlpine et al., "High-Performance Nanowire Electronics and Photonics and Nanoscale Patterning on Flexible Plastic Substrates," *Proc. of the IEEE*, 2005, 93(7):1357-1363.
McAlpine et al., "Nanoimprint Lithogrphy for Hybrid Plastic Electronics," *Nano Letters*, 2003, 3(4):443-445.
McAlpine, et al., "High-Performance Nanowire Electronics and Photonics on Glass and Plastic Substrates," *Nano-Letters*, 2003, 3(11):1531-1535.
Menon, V.P., et al., "Fabrication and Evaluation of Nanoelectrode Ensembles," *Anal. Chem.*, vol.
67, pp. 1920-1928 (1995).
Mizutani, T., et al., "Fabrication and characterization of carbon nanotube FETs," *Proceedings of SPIE*, vol. 5732, pp. 28-36 (2005).
Morales et al., "A Laser Ablation Method for the Synthesis of Crystalline Semiconductor Nanowires," *Science*, 1998, 279: 208-211.
Musin, R.N., et al., "Structural and electronic properties of epitaxial core-shell nanowire heterostructures," *Physical Review*, vol. 71, pp. 155318-1155381-4 (2005).

(56) References Cited

OTHER PUBLICATIONS

Nosho, Y., et al., "n-type carbon nanotube field-effect transistors fabricated by using Ca contact electrodes," *Applied Physics Letters*, vol. 86, pp. 073105 (2005).
Padeste et al., "Modular amperometric immunosensor devices", 8th International Conference on Solid-State Sensors an Actuators and Eurosensors, 1995, 487-490.
Patolsky, F., et al., "Electrical detection of single viruses," *PNAS*, vol. 101, No. 39, pp. 14017-14022 (2004).
Patolsky, F., et al., "Nanowire Nanosensors," *Materials Today*, pp. 20-28 (2005).
Pavesi, L., et al., "Optical gain in silicon nanocrystals," *Nature*, vol. 408, pp. 440-444 (2000).
Qi, P., et al., "Toward Large Arrays of Multiplex Functionalized Carbon Notube Sensors for Highly Sensitive and Selective Molecular Detection," *Nano Letters*, vol. 3, No. 3, pp. 347-351 (2003).
Rueckes et al., "Carbon Nanotube-Based Nonvolatile Random Access Memory for Molecular Computing," *Science*, 2000, 289,:94-97.
Star et al., "Preparation and properties of polymer-wrapped single-walled carbon nanotubes", *Angew. Chem. Int.*, 2001, 40(9): 1721-25.
Takayama et al., "Patterning cells and their environments using multiple laminar fluid flows in capillary networks", *Proc. Natl. Acad. Sci.*, 1999, 96:5545-5548.
Tans et al., "Room-temperature transistor based on a single carbon nanotube," *Nature*, 1998, 393: 49-52.
Thess et al., "Crystalline Ropes of Metallic Carbon Nanotubes," *Science*, 1996, 273:483-487.
Tiefenauer et al., "Towards Amperometric Immunosensor Devices", *Biosensors and Bioelectronics*, 1997, 12: 213-223.
Tong, L., et al., "Subwavelength-diameter silica wires for low-loss optical wave guiding," *Nature*, vol. 426, No. 18, pp. 816-819 (2003).
Urban, J. J., et al., "Single-Crystalline Barium Titanate Nanowires," *Adv. Mater.*, vol. 15, No. 5, pp. 423-426 (2003).
Vossmeyer, T., et al., "Combinatorial approaches toward patterning nanocrystals," *J. Applied Physics*, vol. 84, No. 7, pp. 3664-3670 (1998).
Wang et al., "Highly polarized photoluminescence and photodetection from single indium phosphide nanowires", *Science*, 2001, 293:1455-1457.
Wang et al., "$SiO_2$-enhanced synthesis of Si nanowires by laser ablation," *App. Physics Letters*, 1998, 73(26):3902-3904.
Wang, W. U., et al., "Label-free detection of small-molecule-protein interactions by using nanowire nanosensors," *PNAS*, vol. 102, No. 9, pp. 3208-3212 (2005).
Wei et al., "Synthesis of Single Crystal Bismuth-Telluride and Lead-Telluride Nanowires for New Thermoelectric Materials," *Mat. Res. Soc. Symp. Proc.*, 2000, 581: 219-223.
Whang, D., et al., "Large-Scale Hierarchical Organization of Nanowire Arrays for Integrated Nanysystems," *Nano Letters*, vol. 3, No. 9, pp. 1255-1259 (2003).
Whang, D., et al., "Nanolithography Using Hierarchically Assembled Nanowire Masks," *Nano Letters*, vol. 3, No. 7, pp. 951-954 (2003).
Wolf et al., "Silicon Processing for the VLSI Era," Lattice Press, VI, 2000, 1:12-13.
Wong et al., "Covalently functionalized nanotubes as nanometre-sized probes in chemistry and biology," *Nature*, 1998, 394:52-55.
Wu et al., "Block-by-Block Growth of Single-Crystalline Si/SiGe Superlattice Nanowires," *Nano Letters*. 2002, 2(2): 83-86.
Wu, Y., et al., "Controlled Growth and Structures of Molecular-Scale Silicon Nanowires," *Nano Letters*, vol. 4, No. 3, pp. 433-436 (2004).
Wu, Y., et al., "Single-crystal metallic nanowires and metal/semiconductor nanowire heterostructures," *Nature*, vol. 430, pp. 61-64, (2004).
Xiang, J., et al., "Ge/Si nanowire heterostructures as high-performance field-effect transistors," *Nature*, vol. 441, No. 25, pp. 489-493 (2006).
Yamada, "Analysis of submicron carbon nanotube field-effect transistors," *Appl. Phys. Letters*, 2000, 76: 628-630.
Yang et al., "Controlled Growth of ZnO Nanowires and Their Optical Properties," *Adv. Funct. Mater*, 2002, 12(5): 323-331.
Yang, et al., "Wires on water," *Nature*, vol. 425, pp. 243-244 (2003).
Yu et al., "Nanoscale silicon wires synthesized using simple physical evaporation," *Appl. Phys. Letters*, 1998, 72:3458-3460.
Yun et al., "Ferroelectric Properties of Individual Barium Titanate Nanowires Investigated by Scanned Probe Microscopy," *Nano-Lett*, 2:447-450, 2002.
Zheng, G., et al., "Multiplexed electrical detection of cancer markers with nanowire sensor arrays," *Nature Biotechnology*, vol. 23, No. 10, pp. 1294-1301 (2005).
Zheng, G., et al., "Synthesis and Fabrication of High-Performance n-Type Silicon Nanowire Transistors," *Adv. Mater.*, vol. 16, No. 21, pp. 1890-1893 (2004).
Zhong et al., "Nanowire Crossbar Arrays as Address Decoders for Integrated Nanosystems," *Science*, 2003, 302:1377-1379.
Zhong, et al., "Coherent Single Charge Transport in Molecular-Scale Silicon Nanowires," *Nano Letters*, vol. 5, No. 6, pp. 1143-1146 (2005).
Zhong, Z., et al., "Synthesis of p-Type Gallium Nitride Nanowires for Electric and Photonic Nanodevices," vol. 3, No. 3, pp. 343-346 (2003).
Zhou et al., "Growth morphology and micro-structural aspects of Si nanowires synthesized by laser ablation," *J. of Crystal Growth*, 1999, 197:129-135.
Office Action from U.S. Appl. No. 10/020,004 dated Jan. 15, 2003.
Office Action from U.S. Appl. No. 10/020,004 dated Jun. 25, 2004.
Office Action from U.S. Appl. No. 10/020,004 dated Mar. 14, 2005.
Office Action from U.S. Appl. No. 10/020,004 dated Aug. 30, 2005.
Office Action from U.S. Appl. No. 11/012,549 dated Dec. 20, 2006.
Office Action from U.S. Appl. No. 11/582,167 dated Apr. 23, 2007.
Office Action from U.S. Appl. No. 12/038,794 dated Mar. 6, 2009.
Office Action from U.S. Appl. No. 10/588,833 dated Jun. 12, 2009.
Office Action from U.S. Appl. No. 11/501,466 dated Feb. 5, 2009.
International Search Report and Written Opinion from International Application No. PCT/US2007/006545 mailed Apr. 10, 2008.
International Preliminary Report on Patentability from International Application No. PCT/US2007/006545 mailed Sep. 25, 2008.
Advisory Action mailed May 22, 2014 for U.S. Appl. No. 13/497,852.
Office Action mailed Jun. 24, 2014 for U.S. Appl. No. 13/497,852.
Bradley et al., "Integration of Cell Membranes and Nanotube Transistors," Nano Letters (2005) 5, 841-845.
Fromherz, "Electrical interfacing of nerve cells and semiconductor chips" Chemphyschem—A European Journal of Chemical Physics & Physical Chemistry, Wiley VCH, Weinheim, DE, vol. 3, No. 3, Mar. 12, 2002, pp. 276-284.
Fromherz, "Semiconductor chips with ion channels, nerve cells and brain" Physical E—Low-Dimensional Systems and Nanostructures, Elsevier Science BV, NL, vol. 16, No. 1, Jan. 2003, pp. 24-34.
Gabay et al., "Engineered self-organization of neural networks using carbon nanotube clusters," Physica A (2005) 350,611-621.
James et al., "Extracellular Recordings From Patterned Neuronal Networks Using Planar Microelectrode Arrays," IEEE Trans. Biomed. Eng. (2004) 51, 1640-1648.
Lovat et al., "Carbon Nanotube Substrates Boost Neuronal Electrical Signaling," Nano Letters (2005) 5, 1107-1110.
Merz et al., "Silicon Chip Interfaced with a Geometrically Defined Net of Snail Neurons," Adv Funct Mater (2005) 15, 739-744.
Offenhausser et al., "Field-Effect transistor array for monitoring electrical activity from mammalian neurons in culture," Biosensors & Bioelectronics (1997) 12, 819-826.
Patolsky et al. "Detection, stimulation, and inhibition of neuronal signals with high-density nanowire transistor arrays" Science, vol. 313, Jun. 25, 2006, pp. 1100-1105, XP002474456.
Qing et al., "Nanowire transistor arrays for mapping neural circuits in acute brain slices," PNAS, vol. 107, No. 5, pp. 1882-1887 (Feb. 2, 2010).
Timko et al., "Electronic interface between nanowires and neurons," MRS Abstract, p. 8.23, Apr. 17-21, 2006.
Voelker et al., "Signal Transmission from Individual Mammalian Nerve Cell to Field-Effect Transistor," Small (2005) 1, 206-210.
Office Action mailed Jul. 15, 2014 for U.S. Appl. No. 12/225,142.

* cited by examiner

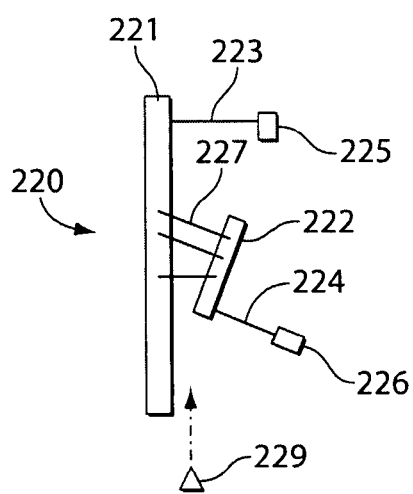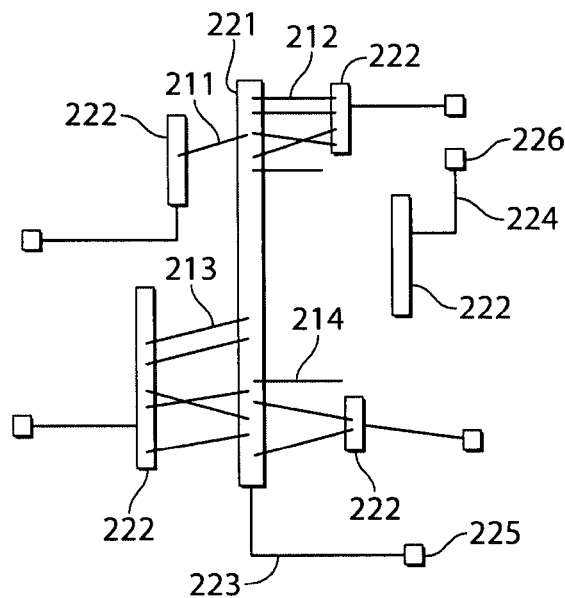
Fig. 6A     Fig. 6B
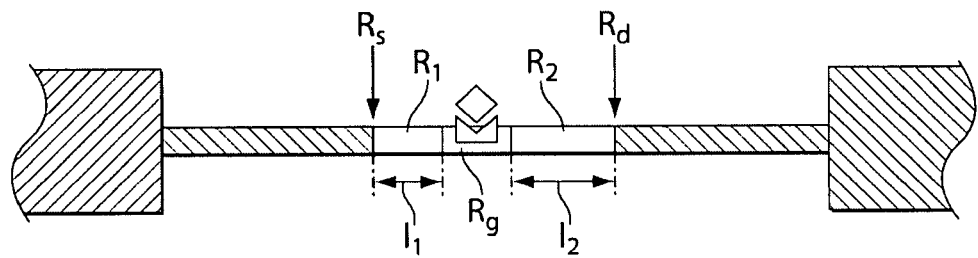
Fig. 7

```
                          SEQUENCE LISTING

<160> NUMBER OF SEQ ID NOS: 6

<210> SEQ ID NO 1
<211> LENGTH: 10
<212> TYPE: DNA
<213> ORGANISM: Artificial Sequence
<220> FEATURE:
<223> OTHER INFORMATION: Synthetic PNA

<400> SEQUENCE: 1
atcatctttg                                                          10

<210> SEQ ID NO 2
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 2
caaagatgat                                                          10

<210> SEQ ID NO 3
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 3
caaacatgat                                                          10

<210> SEQ ID NO 4
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 4
caaacctgat                                                          10

<210> SEQ ID NO 5
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 5
atcaaagatg                                                          10

<210> SEQ ID NO 6
```

```
<211> LENGTH: 10
<212> TYPE: DNA
<213> ORGANISM: Artificial Sequence
<220> FEATURE:
<223> OTHER INFORMATION: Synthetic oligonucleotide sequence

<400> SEQUENCE: 6
tttttttttt                                                              10
```

NANOSENSORS AND RELATED TECHNOLOGIES

RELATED APPLICATIONS

This application is a national phase filing under 35 U.S.C. §371 of International Application No. PCT/US2007/013700, filed Jun. 11, 2007, entitled "Nanosenors and Related Technologies" by Leiber, et al., which claims the benefit of U.S. Provisional Patent Application Ser. No. 60/812,884, filed Jun. 12, 2006, entitled "Nanosensors and Related Technologies," by Lieber, et al., both of which are incorporated herein by reference in their entirety.

GOVERNMENT FUNDING

This invention was made with government support under Grant Nos. FA8650-06-C-7622, FA9550-05-1-0279, and N66001-04-1-8903 awarded by DARPA. The government has certain rights in the invention.

FIELD OF INVENTION

The present invention generally relates to nanotechnology and sub-microelectronic circuitry, as well as associated methods and devices, for example, nanoscale wire devices and methods for use in determining nucleic acids or other analytes suspected to be present in a sample (for example, their presence and/or dynamical information), e.g., at the single molecule level. For example, a nanoscale wire device can be used to detect single base mismatches within a nucleic acid (e.g., by determining association and/or dissociation rates). In some cases, the devices may include metal-semiconductor compounds, such as metal silicides.

BACKGROUND

Interest in nanotechnology, in particular sub-microelectronic technologies such as semiconductor quantum dots and nanowires, has been motivated by the challenges of chemistry and physics at the nanoscale, and by the prospect of utilizing these structures in electronic and related devices. Nanoscopic articles might be well-suited for transport of charge carriers and excitons (e.g. electrons, electron pairs, etc.) and thus may be useful as building blocks in nanoscale electronics applications. Nanowires are well-suited for efficient transport of charge carriers and excitons, and thus are expected to be important building blocks for nanoscale electronics and optoelectronics.

Nanoscale wires having selectively functionalized surfaces have been described in U.S. patent application Ser. No. 10/020,004, entitled "Nanosensors," filed Dec. 11, 2001, published as Publication No. 2002/0117659 on Aug. 29, 2002, and in corresponding International Patent Application Serial No. PCT/US01/48230, filed Dec. 11, 2001, published as International Patent Application Publication No. WO 02/48701 on Jun. 20, 2002 (each incorporated herein by reference). As described, functionalization of the nanoscale wire may permit interaction of the functionalized nanoscale wire with various entities, such as molecular entities, and the interaction induces a change in a property of the functionalized nanowire, which provides a mechanism for a nanoscale sensor device for detecting the presence or absence of an analyte suspected to be present in a sample.

SUMMARY OF THE INVENTION

The present invention generally relates to nanotechnology and sub-microelectronic circuitry, as well as associated methods and devices, for example, nanoscale wire devices and methods for use in determining nucleic acids or other analytes suspected to be present in a sample (for example, their presence and/or dynamical information), e.g., at the single molecule level. For example, a nanoscale wire device can be used to detect single base mismatches within a nucleic acid (e.g., by determining association and/or dissociation rates). The subject matter of the present invention involves, in some cases, interrelated products, alternative solutions to a particular problem, and/or a plurality of different uses of one or more systems and/or articles.

The invention is a method in one aspect. In one set of embodiments, the method includes an act of determining a binding constant and/or a dissociation rate constant between a nucleic acid and a nanoscale wire having immobilized relative thereto a binding partner of the nucleic acid. In another set of embodiments, the method includes an act of determining a binding constant and/or a dissociation rate constant between an analyte and a nanoscale wire having a binding partner of the analyte immobilized relative thereto.

The method, in still another set of embodiments, includes acts of providing a plurality of nucleic acid molecules, each associated with a respective binding partner immobilized relative to a nanoscale wire, dissociating at least some of the plurality of nucleic acid molecules from the respective binding partners, and determining a rate at which the at least some of the plurality of nucleic acid molecules dissociate from the respective binding partners.

According to yet another set of embodiments, the method comprises acts of diffusing at least a portion of a metal into a first portion of a nanoscale wire but not into a second portion of the nanoscale wire, and immobilizing a reaction entity to a second portion of the nanoscale wire.

In still another set of embodiments, the method includes acts of providing a bulk metal adjacent a semiconductor wire, and diffusing at least a portion of the bulk metal into at least a portion of the semiconductor wire in a longitudinal direction along the semiconductor wire for a distance of at least about 10 nm.

According to yet another embodiment, the method includes an act of determining a number of mismatches between an analyte nucleic acid and a binding partner nucleic acid immobilized relative to a binding partner of the nucleic acid.

In another aspect, the invention is an article. The article includes, in one set of embodiments, a nanoscale wire comprising a first portion comprising a metal silicide, and a reaction entity immobilized relative to a second portion of the nanoscale wire having a composition different from the first portion. In another set of embodiments, the article includes a nanoscale wire comprising a first portion comprising a metal silicide, and a second portion having a composition different from the first portion. In some cases, the second portion has a greatest dimension no greater than about 100 nm.

The article, in yet another set of embodiments, includes a nanoscale wire comprising a first portion and a second portion, where the first portion has a binding partner immobilized relative thereto. In some instances, the second portion is free of the binding partner.

Still another aspect of the invention is generally directed to a solution. In some embodiments, the solution includes an analyte, and a nanoscale wire comprising a first portion and a second portion. The second portion may have immobilized relative thereto a binding partner to the analyte, and the first portion may be free of the binding partner. In one embodiment, the analyte has a Debye screening length greater than the greatest dimension of the second portion of the nanoscale wire.

In another aspect, the present invention is directed to a method of making one or more of the embodiments described herein, for example, a sensing device comprising a nanoscale wire. In yet another aspect, the present invention is directed to a method of using one or more of the embodiments described herein, for example, a sensing device comprising a nanoscale wire.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 2A-2K are schematic diagrams illustrating various techniques useful in the fabrication of certain embodiments of the invention;

FIGS. 6A-6B illustrate sensors according to various embodiments of the invention; and FIG. 7 is a schematic diagram of one embodiment of the invention.

BRIEF DESCRIPTION OF THE SEQUENCES

Figure 1A:
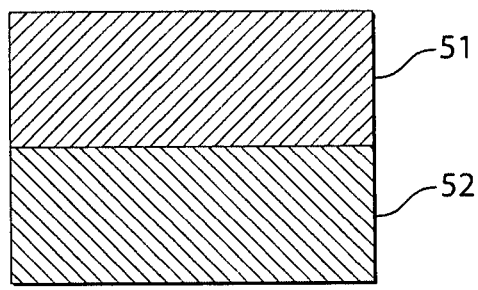
FIGS. 1A-1E are schematic diagrams illustrating various embodiments of the invention.

SEQ ID NO: 1 is ATCATCTTTG, a synthetic PNA sequence;

SEQ ID NO: 2 is CAAAGATGAT, a synthetic DNA sequence;

SEQ ID NO: 3 is CAAACATGAT, a synthetic DNA sequence;

SEQ ID NO: 4 is CAAACCTGAT, a synthetic DNA sequence;

SEQ ID NO: 5 is ATCAAAGATG, a synthetic DNA sequence;

SEQ ID NO: 6 is TTTTTTTTTT, a synthetic DNA sequence;

SEQ ID NO: 7 is CAAAGATG, a portion of SEQ ID NO: 5; and

SEQ ID NO: 8 is CATCTTTG, a portion of SEQ ID NO: 1.

DETAILED DESCRIPTION

The present invention generally relates to nanotechnology and sub-microelectronic circuitry, as well as associated methods and devices, for example, nanoscale wire devices and methods for use in determining nucleic acids or other analytes suspected to be present in a sample (for example, their presence and/or dynamical information), e.g., at the single molecule level. For example, a nanoscale wire device can be used in some cases to detect single base mismatches within a nucleic acid (e.g., by determining association and/or dissociation rates). In one aspect, dynamical information such as a binding constant, an association rate, and/or a dissociation rate, can be determined between a nucleic acid or other analyte, and a binding partner immobilized relative to a nanoscale wire. In some cases, the nanoscale wire includes a first portion comprising a metal-semiconductor compound, and a second portion that does not include a metal-semiconductor compound. The binding partner, in some embodiments, is immobilized relative to at least the second portion of the nanoscale wire, and the size of the second portion of the nanoscale wire may be minimized and/or controlled in certain instances. Articles and devices of size greater than the nanoscale are also included in some embodiments. Still other aspects of the invention include assays, sensors, kits, and/or other devices that include such nanoscale wires, methods of making and/or using such nanoscale wires, or the like.

One aspect of the invention is generally directed to determining dynamical information, for example, a binding constant, and/or an association and/or a dissociation rate constant between an analyte, such as a nucleic acid, and a nanoscale wire having immobilized relative thereto a binding partner to the analyte. The nanoscale wire may be (or comprise), for example, a nanotube or a nanowire, e.g., a semiconductor nanowire, a metal nanowire, a metal-semiconductor nanowire (e.g., a metal silicide nanowire), etc., as discussed in greater detail below. In one set of embodiments, the analyte (i.e., the substance to be determined using the nanoscale wire) is a nucleic acid, for example, DNA, RNA, PNA, or the like, as well as combinations thereof. The binding partner may also be a nucleic acid that is substantially or perfectly complementary to the analyte nucleic acid. However, in other embodiments, binding partners other than nucleic acids may be used (for example, an enzyme able to recognize the analyte nucleic acid), as described below. The nanoscale wire may also have a plurality of binding partners immobilized relative thereto, which may each independently be the same or different (e.g., multiple, substantially identical copies of the same nucleic acid sequence, and/or different nucleic acid sequences, and/or combinations thereof). In some embodiments, the analyte can be determined with a high degree of sensitivity, and in some cases even a single molecule of analyte can be determined.

A nucleic acid typically has a plurality of bases, connected via a polymer backbone. Non-limiting examples of nucleic acids include RNA (ribonucleic acid), DNA (deoxyribonucleic acid), or PNA (peptide nucleic acid). Typically, a nucleic acid includes multiple nucleotides, for example, adenosine ("A"), guanosine ("G"), thymine ("T"), uridine ("U"), or cytidine ("C"). Nucleotides often are formed from molecules comprising a sugar (e.g. ribose or deoxyribose)

linked to a phosphate group and an exchangeable organic base (although a PNA has a different backbone, i.e., one comprising peptide linkages). A sugar (or peptide) and a base (without the phosphate) together form a nucleoside. Examples of organic bases include, but are not limited to, various pyrimidines or purines.

In one set of embodiments, the binding partner is a nucleic acid (or contains a nucleic acid sequence) that is substantially or perfectly complementary to the analyte nucleic acid (or a portion thereof). As used herein, a first portion of a nucleic acid is "complementary" to a second portion of a nucleic acid if the nucleotides of the first portion and the nucleotides of the second portion are generally complementary (i.e., Watson-Crick pairing, A to T or U, C to G, etc.). Typically, the nucleic acids have enough complementarity that the nucleic acids are able to specifically bind together in a defined, predictable orientation. In some cases, the nucleic acid portions are at least 80%, at least 85%, at least 90%, at least 95%; at least 96%, at least 97%, at least 98%, or at least 99% complementary. Perfectly complementary nucleic acids are 100% complementary. In some embodiments, the first and second portions have a maximum of 0, 1, 2, 3, 4, 5, 6, 7, 8, 9, or 10 nucleotide mismatches, and in some instances the number of mismatches between the nucleic acids may be determined, e.g., as discussed herein. A non-limiting example of nucleic acids having nucleotide mismatches are SNPs, or single nucleotide polymorphisms, which are well-known to those of ordinary skill in the art. The complementary portions of the nucleic acids may be at least 5 nucleotides in length, and in some cases, at least 7 nucleotides in length, at least about 10 nucleotides in length, at least about 12 nucleotides in length, at least about 15 nucleotides in length, at least about 20 nucleotides in length, at least about 25 nucleotides in length, at least about 50 nucleotides in length, etc.

In some embodiments, association or binding of an analyte (e.g., a nucleic acid) to a binding partner may alter a property of the nanoscale wire, for example, an electrical property such as the conductivity of the nanoscale wire, e.g., if the analyte is charged. As a non-limiting example, a negatively charged analyte, such as a nucleic acid, that to associates with a binding partner and becomes immobilized with respect to a p-type nanoscale wire may increase the conductance of the p-type nanoscale wire (or decrease the conductance of an n-type nanoscale wire). Similarly, a positively charged analyte would increase the conductance of an n-type nanoscale wire, or decrease the conductance of a p-type nanoscale wire. Such conductance changes are typically reversible, i.e., if the analyte subsequently dissociates or unbinds from the binding partner, the nanoscale wire generally returns to its original conductance. A determination of the conductivity or other property of the nanoscale wire, and/or a change in such conductivity or other property can thus allow determination of the association and/or dissociation of the analyte with the binding partner.

In one embodiment, a conductance (or a change in conductance) of less than about 1 nanosiemens (nS) in a nanoscale wire sensor of the invention can be detected. In another embodiment, a conductance in the range of thousandths of nS can be detected. In other embodiments, conductances of less than about 10 microsiemens, less than about 1 microsiemens, less than about 100 nS, or less than about 10 nS can be detected. The concentration of a species, or analyte, may be detected from femtomolar concentrations, to nanomolar, micromolar, millimolar, and to molar concentrations and above. By using nanoscale wires with known detectors, sensitivity can be extended to single molecules in some cases, as discussed herein. As a non-limiting example, differences between a first nucleic acid (such as DNA) and a second nucleic acid having a difference of a single base may be determined using certain embodiments of the invention, e.g., at the single molecule level, as discussed in more detail below.

As another non-limiting example, a charged analyte, such as a nucleic acid, may be determined by determining a change in an electrical property of the nanoscale wire, for example, voltage, current, conductivity, resistivity, inductance, impedance, electrical change, an electromagnetic change, etc. Immobilizing a charged analyte relative to the nanoscale wire may cause a change in the conductivity of the nanoscale wire, and in some cases, the distance between the charged analyte and the nanoscale wire may determine the magnitude of the change in conductivity of the nanoscale wire.

In certain cases, additional properties of an analyte may be determined based on the association of the analyte with the binding partner. For instance, the rate of association and/or dissociation of the analyte to the binding partner may be determined using the nanoscale wire. In some cases, a binding constant of the association may be determined. The binding constant is, generally speaking, a measure of the ratio between the respective rates of association and dissociation of the analyte to the binding partner.

As a non-limiting example, the analyte and the binding partner can each be nucleic acids (which can be of the same type, or of different types), and dynamical information, such as a binding constant, an association rate, and/or a dissociation rate may be determined between the nucleic acids using the nanoscale wire. In certain embodiments, the binding constant and/or the dissociation rate may be sensitive to the number of mismatches between the analyte nucleic acid and its binding partner nucleic acid. For example, if one or more mismatches are present, then the relative rates of dissociation may be substantially different, relative to perfectly complementary nucleic acids. Accordingly, even relatively small numbers of mismatches (e.g., 5 or less, 4 or less, 3 or less, 2 or less, or 1 or less) may be detected using various embodiments of the invention, and in some cases, a single nucleotide mismatch of a single molecule may be determined using a nanoscale wire of the invention. Thus, in another aspect of the invention, a nanoscale wire may be used to determine mismatches between two nucleic acids of the invention, for example, between a first nucleic acid, immobilized relative to a nanoscale wire (or a portion thereof), and a second nucleic acid (i.e., an analyte molecule) that is substantially or perfectly complementary to the first nucleic acid. Additionally, as discussed herein, in some cases, single nucleic acid molecules (i.e., a first nucleic acid molecule and a second nucleic acid molecule) may be determined, including possible mismatches between the first and second nucleic acid molecules.

The rates of association and/or dissociation, and/or the binding constant of the analyte with respect to the binding partner, and/or the determination of mismatches in complementary nucleic acids, may be determined using any suitable technique. In one set of embodiments, the conductivity of the nanoscale wire is measured as a function of time, for instance, by using the nanoscale wire within a field effect transistor ("FET") to measure conductivity. Those of ordinary skill in the art will be aware of FETs and how to make and use them. For instance, an alternating current ("AC") signal may be used through a FET in some instances to determine association and/or dissociation of an analyte with a binding partner, for example, an AC signal having an amplitude of between 10 mV and 30 mV, and/or a frequency of between 17 Hz and 500 Hz. The conductivity of the nanoscale wire may change in discrete or measurable increments, corresponding to the association and/or dissociation of individual analyte molecules to the binding partners immobilized with respect to the nanoscale wire, and such changes may be used to determine the rates of association and/or dissociation (or binding/unbinding). Typically, such rates are quantified using measures such as "rate constants" and similar parameters, as are known to those of ordinary skill in the art (e.g., $k_{on}$ and $k_{off}$).

Interaction of the analyte with the binding partner may cause a detectable change or modulation in a property of the nanoscale wire, for example, through electrical coupling with the binding partner. The term "electrically coupled" or "electrocoupling," when used with reference to an analyte and a binding partner, refers to an association between any of the analyte, binding partner, and/or the nanoscale wire such that electrons can move from one to the other, or in which an electrical characteristic (or a change in the electrical characteristic) of one can be determined by one of the others (e.g., through capacitance coupling, transient imbalances in ion concentration, or the like). This can include electron flow between these entities, or a change in a state of charge, oxidation, or the like, that can be determined by the nanoscale wire. As examples, electrical coupling or immobilization can include direct covalent linkage between the analyte and the nanoscale wire, indirect covalent coupling (for instance, via a linker, and/or a plurality of linkers, e.g., serially), direct or indirect ionic bonding between the analyte and the nanoscale wire, direct or indirect bonding of both the analyte and the nanoscale wire to a particle (i.e., the particle acts as a linker between the analyte and the nanoscale wire), direct or indirect bonding of both the analyte and the nanoscale wire to a common surface (i.e., the surface acts as a linker), and/or other types of bonding or interactions (e.g. hydrophobic interactions or hydrogen bonding). In some cases, no actual covalent bonding is required; for example, the analyte or other moiety may simply be contacted with the nanoscale wire surface. There also need not necessarily be any contact between the nanoscale wire and the analyte or other moiety where the nanoscale wire is sufficiently close to the analyte to permit electron tunneling or other effects between the analyte and the nanoscale wire.

Thus, the binding partner may be immobilized relative to the nanoscale wire to cause a detectable change in the nanoscale wire. In some cases, the binding partner is positioned within about 100 nm of the nanoscale wire, within about 75 nm of the nanoscale wire, within about 50 nm of the nanoscale wire, within about 20 nm of the nanoscale wire, within about 15 nm of the nanoscale wire, or within about 10 nm of the nanoscale wire. The actual proximity can be determined by those of ordinary skill in the art. In some cases, the binding partner is positioned less than about 5 nm from the nanoscale wire. In other cases, the binding partner is positioned within about 4 nm, within about 3 nm, within about 2 nm, or within about 1 nm of the nanoscale wire.

In some embodiments, the binding partner is fastened to or directly bonded (e.g., covalently) to the nanoscale wire, e.g., as further described herein. However, in other embodiments, the binding partner is not directly bonded to the nanoscale wire, but is otherwise immobilized relative to the nanoscale wire, i.e., the binding partner is indirectly immobilized relative to the nanoscale wire, as discussed above. For instance, the binding partner may be attached to the nanoscale wire through a linker, i.e., a species (or plurality of species) to which the binding partner and the nanoscale wire are each immobilized relative thereto, e.g., covalently or non-covalently bound to. As an example, a linker may be directly bonded to the nanoscale wire, and the binding partner may be directly bonded to the linker, or the binding partner may not be directly bonded to the linker, but immobilized relative to the linker, e.g., through the use of non-covalent bonds such as hydrogen bonding (e.g., as in complementary nucleic acid-nucleic acid interactions), hydrophobic interactions (e.g., between hydrocarbon chains), entropic interactions, or the like. The linker may or may not be directly bonded (e.g., covalently) to the nanoscale wire.

Non-limiting examples of chemistries suitable for immobilizing binding partners relative to nanoscale wires, optionally via one or more linkers, include the following. In one set of embodiments, the surface of the nanoscale wire may be functionalized. For example, the surface may be functionalized with aldehydes, amines, thiols, or the like, which may form nitrogen-containing or sulfur-containing covalent bonds. In some embodiments, for instance, the binding partner may be covalently bound to the nanoscale wire through the use of a moiety such as an aldehyde moiety, an amine moiety, and/or a thiol moiety.

In certain embodiments, a nanoscale wire is reacted with an aldehyde, amine, and/or a thiol to functionalize the nanoscale wire with the appropriate moiety, e.g., such that the surface of the nanoscale wire includes terminal aldehyde, amine, and/or thiol groups (for example, as a monolayer). In some embodiments, a solution may contain a silane comprising an aldehyde moiety, for example, aldehydes such as aldehyde propyltrimethoxysilane (($CH_3O)_3SiCH_2CH_2CHO$), or other aldehydes, for instance, having a formula such as $(OCHR^1)(R^2O)(R^3O)(R^4O)Si$, $(OCHR^1)R^2R^3XSi$, $(OCHR^1)R^2X^1X^2Si$, or $(OCHR^1)X^1X^2X^3Si$, where each R is independently an alkyl or other carbon-containing moiety, a silane comprising an amine moiety, a silane comprising a thiol moiety, etc.; and each X is independently a halogen. All, or only a portion of, the surface of the nanoscale wire may be functionalized, for instance, with aldehyde moieties (for example, a portion of the nanoscale wire may be blocked or shielded, prior to aldehydization of the surface).

Additional non-limiting examples of suitable amines or thiols include amino- and thiol-functionalized silane derivatives, for instance, trimethoxy propylamine silane (($CH_3O)_3SiCH_2CH_2CH_2NH_2$) or propylthiol trimethoxy silane (($CH_3O)_3SiCH_2CH_2CH_2SH$), which may react with all, or only a portion of, the surface of the nanoscale wire to form, surfaces functionalized with, respectively, amines or thiols. Other potentially suitable amines may have a formula $(Z^1Z^2NR^1)(R^2O)(R^3O)(R^4O)Si$, where each R is independently an alkyl or other carbon-containing moiety and each Z independently is —H or an alkyl or other carbon-containing moiety; other potentially suitable thiols may have a formula $(HSR^1)(R^2O)(R^3O)(R^4O)Si$. In some cases, the derivative may have more than one functional group, for example, the derivative may have an amine and a thiol group, an amine and an aldehyde group, a thiol and an aldehyde group, etc.

One or more binding partners, e.g., nucleic acids, proteins, enzymes, antibodies, receptors, ligands, etc., may be reacted with the aldehyde, amine, and/or thiol moieties to covalently bind the binding partner to the nanoscale wire. For instance, a nucleic acid or other binding partner may be modified with an amine group or a maleimide group. The binding partner may then be immobilized with respect to the surface via reaction between the amine and an aldehyde or epoxy, between the maleimide group and a thiol, etc.

In some cases, after the binding partner has been fastened to the nanoscale wire, the surface of the nanoscale wire, including any unreacted moieties, is then passivated, e.g., blocked with one or more compounds that causes the moieties to become unreactive. Non-limiting examples of such passivating agents include ethanolamine, e.g., to block unreacted aldehyde groups. For example, a solution may be added to the nanowires that includes one or more passivating agents.

Additional non-limiting examples of chemistries suitable for attaching binding partners to nanoscale wires are disclosed in U.S. Provisional Patent Application Ser. No. 60/707,136, filed Aug. 9, 2005, entitled "Nanoscale Sensors," by Lieber, et al., incorporated herein by reference.

The invention, in some embodiments, involves a sensing element (which can be an electronic sensing element) comprising a sample exposure region and a nanoscale wire able to detect the presence or absence of an analyte, and/or the concentration of the analyte, in a sample (e.g. a fluid sample) containing, or suspected of containing, the analyte, and/or to determine dynamic information, e.g., association and/or dissociation of the analyte with the binding partner (for instance, association rate, dissociation rate, binding constant, rate constant, etc.). The "sample exposure region" may be any region in close proximity to the nanoscale Wire where a sample in the sample exposure region addresses at least a portion of the nanoscale wire. Examples of sample exposure regions include, but are not limited to, a well, a channel, a microfluidic channel, or a gel. In certain embodiments, the sample exposure region is able to hold a sample proximate the nanoscale wire, and/or may direct a sample toward the nanoscale wire for determination of an analyte in the sample. The nanoscale wire may be positioned adjacent or within the sample exposure region. Alternatively, the nanoscale wire may be a probe that is inserted into a fluid or fluid flow path. The nanoscale wire probe may also comprise, in some instances, a microneedle that supports and/or is integral with the nanoscale wire, and the sample exposure region may be addressable by the microneedle. In this arrangement, a device that is constructed and arranged for insertion of a microneedle probe into a sample can include a region surrounding or otherwise in contact with the microneedle that defines the sample exposure region, and a sample in the sample exposure region is addressable by the nanoscale wire, and vice versa. Fluid flow channels can be created at a size and scale advantageous for use in the invention (e.g., microchannels) using a variety of techniques such as those described in International Patent Application Serial No. PCT/US97/04005, entitled "Method of Forming Articles and Patterning Surfaces via Capillary Micromolding," filed Mar. 14, 1997, published as International Patent Application Publication No. WO 97/33737 on Sep. 18, 1997, and incorporated herein by reference.

As a non-limiting example, a sample, such as a fluid suspected of containing an analyte that is to be determined, may be presented to a sample exposure region of a sensing element comprising a nanoscale wire. An analyte present in the fluid that is able to bind to the nanoscale wire and/or a binding partner immobilized relative to the nanoscale wire may cause a change in a property of the nanoscale wire that is determinable upon binding, e.g. using conventional electronics. If the analyte is not present in the fluid, the relevant property of the nanoscale wire will remain substantially unchanged, and the detector will measure no significant change. Thus, according to this particular example, the presence or absence of an analyte can be determined by monitoring changes, or lack thereof, in the property of the nanoscale wire. In some cases, if the detector measures a change, the magnitude of the change may be a function of the concentration of the analyte, and/or a function of some other relevant property of the analyte (e.g., charge or size, etc.). Thus, by determining the change in the property of the nanoscale wire, the concentration or other property of the analyte in the sample may be determined.

A "fluid," as used herein, generally refers to a substance that tends to flow and to conform to the outline of its container. Typically, fluids are materials that are unable to withstand a static shear stress. When a shear stress is applied to a fluid, it experiences a continuing and permanent distortion. Typical fluids include liquids and gases, but may also include free-flowing solid particles, viscoelastic fluids, and the like.

Where a detector is present, any detector capable of determining a property associated with a nanoscale wire can be used, which can be used to determine the analyte. The property can be electronic, optical, or the like. An electronic property of a nanoscale wire can be, for example, its conductivity, resistivity, etc, as previously described. For example, the detector can be constructed for measuring a change in an electronic or magnetic property (e.g. voltage, current, conductivity, resistance, impedance, inductance, charge, etc.). The detector typically includes a power source and a voltmeter and/or an ammeter. In one embodiment, a conductance less than 1 nS can be detected. In some cases, a conductance in the range of thousandths of nS can be detected. The concentration of a species, or analyte, may be detected from less than micromolar to molar concentrations and above. By using nanoscale wires with known detectors, sensitivity can be extended to a single molecule, and/or a single mismatch within a single nucleic acid molecule.

As another example, one or more different nanoscale wires may cross the same microfluidic channel (e.g., at different positions) to detect the same or different analytes, to measure a flowrate of an analyte(s), etc. In another embodiment, one or more nanoscale wires may be positioned in a microfluidic channel to form one of a plurality of analytic elements, for instance, in a microneedle probe, a dip and read probe, etc. The analytic elements probe may be implantable and capable of detecting several analytes simultaneously in real time, according to certain embodiments. In another embodiment, one or more nanoscale wires may be positioned in a microfluidic channel to form an analytic element in a microarray for a cassette or a lab-on-a-chip device. Those of ordinary skill in the art would know of examples of cassette or lab-on-a-chip devices that are suitable for high-throughout chemical analysis and screening, combinational drug discovery, etc.

Another set of embodiments of the present invention provides an article comprising one or more nanoscale wires and a detector constructed and arranged to determine a change in an electrical property of the nanoscale wire. For example, at least a portion of the nanoscale wires (which may be aligned in some cases) is addressable by a sample containing, or suspected of containing, an analyte. The phrase "addressable by a fluid" is defined as the ability of the fluid to be positioned relative to the nanoscale wire so that an analyte suspected of being in the fluid is able to interact with the nanoscale wire. The fluid may be proximate to or in contact with the nanoscale wire.

Additional examples of such systems, and techniques for using such systems (e.g., for detecting "false positive" events, for detecting multiple analytes simultaneously and/or sequentially, for detecting date in real time and/or near-real time, for detecting analyte binding as a function of time, for use of arrays and/or cassettes containing multiple nanoscale wires, for computer control and/or integrated devices, etc.), are disclosed in U.S. patent application Ser. No. 11/137,784, filed May 25, 2005, entitled "Nanoscale Sensors," by Lieber, et al.; U.S. Provisional Patent Application Ser. No. 60/790, 322, filed Apr. 7, 2006, entitled "Nanoscale Wire Methods and Devices," by Lieber, et al.; or U.S. Provisional Patent Application Ser. No. 60/707,136, filed Aug. 9, 2005, entitled "Nanoscale Sensors," by Lieber, et al., each incorporated herein by reference.

Certain aspects of the invention are directed to techniques for fabricating nanoscale wires, e.g., containing portions to which binding partners or other reaction entities may be immobilized relative thereto. The criteria for selection of nanoscale wires and other conductors or semiconductors for use in the invention are based, in some instances, upon whether the nanoscale wire itself is able to interact with an analyte, whether the appropriate binding partner can be easily attached to the surface of the nanoscale wire, and/or whether the appropriate binding partner is near the surface of the nanoscale wire. Selection of suitable conductors or semiconductors, including nanoscale wires, will be apparent and readily reproducible by those of ordinary skill in the art with the benefit of the present disclosure.

In one aspect, the present invention provides a method of preparing a nanostructure. In one set of embodiments, the method involves allowing a first material to diffuse into at least part of a second material, optionally creating a new compound. For example, the first and second materials may each be metals or semiconductors, one material may be a metal and the other material may be a semiconductor (e.g., creating a metal-semiconductor compound), etc. In one set of embodiments, a semiconductor may be annealed to a metal. For example, a portion of the semiconductor and/or a portion of the metal may be heated such that at least some metal atoms are able to diffuse into the semiconductor, or vice versa. In one embodiment, a metal electrode (e.g., a nickel, gold, copper, silver, chromium electrode, etc.), may be positioned in physical contact with a semiconductor nanoscopic wire, and then annealed such that at least a portion of the semiconductor diffuses into at least a portion of the metal, optionally forming a metal-semiconductor compound, e.g., as disclosed in International Patent Application No. PCT/US2005/004459, filed Feb. 14, 2005, entitled "Nanostructures Containing Metal-Semiconductor Compounds," published as WO 2005/093831 on Oct. 6, 2005 by Lieber, et al., or U.S. Provisional Patent Application Ser. No. 60/707,136, filed Aug. 9, 2005, entitled "Nanoscale Sensors," by Lieber, et al., each incorporated herein by reference. For example, the semiconductor may be annealed with the metal at a temperature of about 300° C., about 350° C., about 400° C., about 450° C., about 500° C., about 550° C., about 600° C., etc., for a period of time of at least about 30 minutes, at least about 1 hour, at least about 2 hours, at least about 4 hours, at least about 6 hours, etc. Such annealing may allow, for example, lower contact resistances or impedances between the metal and the semiconductor.

As used herein, a "metal-semiconductor compound" is a compound that includes at least one metal combined with a semiconductor. In metal-semiconductor compounds of the invention, at least one portion of the compound includes a metal and a semiconductor present in a stoichiometrically defined ratio, i.e., the metal atoms and the semiconductor atoms are present within the compound (i.e., on the atomic scale) in a whole number ratio that is chemically defined, i.e., defined on the basis of the atomic interactions between the metal atoms and the semiconductor atoms within the compound that lead to a ratio of elements present dictated by the bonding principles of chemistry (e.g. coordination chemistry, atomic and molecular orbital interactions and formation, crystal packing, and/or the like). This is to be distinguished from alloys or mixtures, which are simply blends of two or more atoms in a substance, in which the atoms can be mixed together in any ratio, where the ratio is not determined by stoichiometric interactions between the atoms, and doping, where, e.g., ion bombardment of a material with a dopant leads to non-stoichiometric amounts of the dopant in the host material dictated by the amount of dopant introduced. Instead, the metal atoms and the semiconductor atoms in a metal-semiconductor compound interact on the atomic level in a defined fashion, thus resulting in the metal-semiconductor compound having a whole number ratio between the metal atoms and the semiconductor atoms within the compound, i.e., the ratio is dictated by atomic interactions between the metal atoms and the semiconductor atoms within the compound. Thus, the stoichiometric ratio between the metal atoms and the semiconductor atoms is always the same on the atomic level (i.e., at any location within the compound). As an example, there may be ionic charged interactions between the metal atoms and the semiconductor atoms such that, for charge neutrality, there is a stoichiometric ratio between the metal atoms and the semiconductor atoms within the compound, for example, $MZ$, $M_2Z$, $M_2Z_3$, $MZ_2$, $M_3Z_2$, or the like, where M is a metal and Z is a semiconductor. A specific non-limiting example is nickel silicide, $NiSi$. In some cases, more than one type of metal atom and/or more than one type of semiconductor atom may be present in the metal-semiconductor compound. It should be recognized, of course, that measurements of the ratio of two or more atoms in a compound are not necessarily always exact, due to experimental error and other practical limitations. Thus, in some cases, the ratio so measured may be stoichiometric in reality, even though the experimental measurements deviate somewhat from whole number ratios. As an example, the actual ratios determined for a metal-semiconductor compound may be within about 10% or about 5% of a stoichiometric, whole number ratio.

In one set of embodiments, the metal within the metal-semiconductor compound is a transition metal, for example, an element from one or more of Group IB, Group IIB, Group IIIB, Group IVB, Group VB, Group VIB, Group VIIB, or Group VIIIB. In some cases, Group VIIIB metals may be particularly useful within the metal-semiconductor compound, for example, nickel, iron, palladium, platinum, iridium, etc.

Figure 1B:
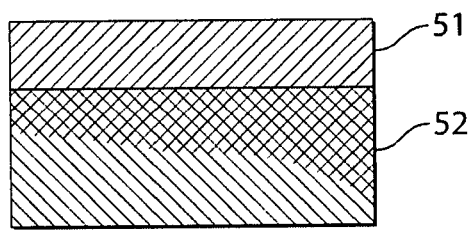
Figure 1C:
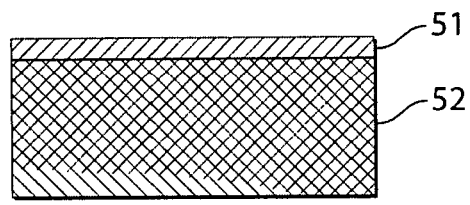

In one embodiment, a first material is positioned adjacent or proximate to a second material (by known forms of deposition, for example), and the atoms of the first material are allowed to diffuse into at least a portion of the second material. At least one of the first and second materials may be a nanoscale material. Thus, as an example, in FIG. 1A, a first material 51 is positioned next to a second material 52. The first material may be positioned such that it contacts the second material, and/or such that atoms from the first material are able to diffuse into the second material (for example, an intervening material or space may be present between the first material and the second material). Diffusion of the first material into at least a portion of the second material is then allowed to occur, as shown in FIG. 1B. When sufficient diffusion has occurred (i.e., when a desired amount of the first material has diffused into the second material), the first material (or at least a portion thereof) may optionally be removed, as is shown in FIG. 1C. In a nanoscale wire, the diffusion may be axial and/or longitudinal along the nanoscale wire, and in some cases, the diffusion rate (e.g., in either or both directions) may be controlled by controlling the size or diameter of the nanoscale wires. For instance, in some cases, thinner nanoscale wires may result in higher diffusion rates.

As an example, to create a nanoscale wire comprising a metal-semiconductor compound, a metal may be positioned adjacent or proximate to a semiconductor (by known forms of deposition, for example), and the metal atoms allowed to diffuse into at least a portion of the semiconductor material, for example, to create one or more heterojunctions within the nanoscale wire. The metal may be a bulk metal in some cases, i.e., a metal having a volume of at least nanoscopic dimensions (e.g., having a smallest dimension of at least about 1 nm).

In some cases, diffusion of the metal atoms into the semiconductor may be initiated and/or facilitated, for example, by the application of high pressures and/or high temperatures, for example, temperatures of at least about 500° C., at least about 550° C., at least about 600° C., at least about 700° C., or more in some cases. The diffusion rate may be controlled by the annealing temperature and/or the time of annealing, and the amount and/or length of diffusion can be readily optimized for a particular application using routine experimentation. In certain instances, substantial diffusion of metal atoms into the semiconductor may not substantially occur absent an increase or an alteration in the temperature and/or pressure. In some cases, diffusion of the metal atoms into the semiconductor (or at least a portion thereof) may proceed until a metal-semiconductor compound forms (e.g., through a chemical reaction), and/or when a stoichiometric ratio of metal atoms to semiconductor atoms has been established. As a particular example, if the metal is a transition metal such as nickel, and the semiconductor material is a silicon nanoscale wire, diffusion of nickel into the silicon nanoscale wire may proceed until the silicon nanoscale wire (or at least that portion of the nanoscale wire exposed to nickel) has been converted into nickel silicide. In other cases, however, the metal atoms and the semiconductor atoms may not be in a stoichiometric ratio. In certain instances, diffusion of the metal into the semiconductor may be stopped before metal-semiconductor compound formation or stoichiometric equilibrium has been established; thus, in one embodiment, the nanoscale wire may include a non-stoichiometric ratio of metal atoms to semiconductor atoms. The diffusion of the metal into the semiconductor may be determined using techniques known to those of ordinary skill in the art, such as SEM, TEM, AFM, EFM, etc.

After the metal atoms have been allowed to diffuse into the semiconductor, in some cases, excess metal may be removed from the semiconductor, for example, by the application of certain species such as metal etchants. For example, if the metal diffused into the semiconductor is nickel, a suitable metal etchant may include acids such as nitric acid, sulfuric acid, hydrochloric acid, and/or nickel etchants such as TFB or TFG (available from Transene, Danvers, Mass.). In some cases, the removal of the excess metal from the semiconductor may be facilitated by elevated temperatures and/or pressures.

Figure 1D:
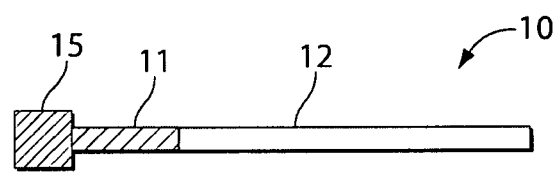

Thus, in one embodiment, a nanoscale wire may be prepared having a first portion, defined by diffusion of a metal into the nanoscale wire, and a second portion that the metal did not diffuse into. For example, as illustrated in FIG. 1D, a semiconductor 10 having first and second portions may be prepared by exposing a portion of the nanoscale wire to a metal 15, and allowing the metal ions to diffuse into the semiconductor to create a first portion 11 and a second portion 12. The first portion 11 may be defined by the diffusion of the metal into the semiconductor, while the second portion 12 may be defined by portions of the semiconductor free of the metal, and such portions may be radially and/or longitudinally positioned along the nanoscale wire.

The size of the portions may be controlled, for instance, by controlling the temperature of the semiconductor and/or the annealing time. For instance, by heating the nanoscale wire to diffuse the metal into the semiconductor, then cooling the nanoscale wire once the metal has diffused a predetermined distance into the semiconductor, the size of the second portion may be controlled as desired. For example, referring to FIG. 1D, the size of first portion 11 of the semiconductor may be no greater than about 900 nm, than about 750 nm, than about 500 nm, than about 300 nm, than about 100 nm, than about 50 nm, than about 30 nm, than about 10 nm, etc., away from metal 15; and/or the size of second portion 12 of the semiconductor may be no greater than about 900 nm, than about 750 nm, than about 500 nm, than about 300 nm, than about 100 nm, than about 50 nm, than about 30 nm, than about 10 nm, etc. In some cases, first and/or second portions may be measured relative to the overall length of semiconductor 10, e.g., measured from metal 15. For instance, diffusion of the metal may occur within semiconductor 10 such that less than about 10%, less than about 20%, less than about 30%, less than about 40%, less than about 50%, less than about 60%, less than about 70%, less than about 80%, less than about 90%, etc. of the semiconductor comprises the first region.

As previously mentioned, the diffusion of the metal atoms into the semiconductor may be facilitated, for example, by the application of high pressures and/or high temperatures, for example, temperatures of at least about 500° C., at least about 550° C., at least about 600° C., at least about 700° C., or more in some cases. In certain instances, substantial diffusion of metal atoms into the semiconductor may not substantially occur absent an increase or an alteration in the temperature and/or pressure.

Figure 1E:
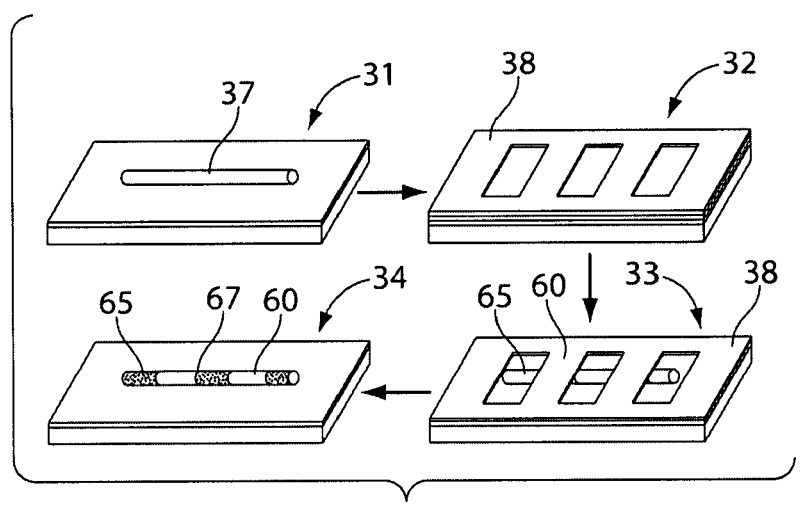

In another set of embodiments, a nanostructure can be prepared by exposing a portion of the second material to the first material. The first material can diffuse into regions of the second material that are adjacent or proximate the first material, while regions of the second material not adjacent or proximate the first material will remain substantially free of the first material. As one example, as shown in FIG. 1E, a mask 38 may be patterned on a nanostructure 37 (or other nanostructure) to define one or more regions where the nanostructure is covered by the mask 60 and one or more regions where the nanostructure is free of the mask 65. The mask may have any pattern defined therein, and can define 2- or 3-dimensional patterns on the nanostructure, depending on the specific application. Any suitable material may be used to form the mask, for instance, a photoresist may be formed on the nanostructure to define a mask, e.g., through photolithographic techniques known to those of ordinary skill in the art. As a non-limiting example, a mask with a series of openings may be formed on a nanowire to create a series of heterojunctions along the nanowire, or if not formed on the nanowire (or other nanostructure), positioned in proximity relative to the nanowire so as to be able to mask application of material on the nanowire. As another example, a mask may be formed from a nanoscale wire, for example, a nanoscale wire, a nanotube, a core/shell nanoscale wire, etc. For instance, the nanoscale wire used as a mask may be placed on or positioned in proximity to the nanowire (or other nanostructure); the nanoscale wire used as a mask may thus mask application of material on the nanowire.

After positioning of the mask on the second material of the nanostructure, or between the nanostructure and the source of material to be deposited thereto, the first material may be deposited on the mask. Regions of the nanostructure that are free of the mask 65 will have the first material deposited thereon, while regions of the nanostructure covered by the mask 60 will not be exposed to the first material. The first material can then diffuse into the portions second material adjacent or proximate the first material. The mask may be removed before or after diffusion of the first material into portions of the second material. After diffusion, a nanostructure having one or more heterojunctions 67, defined by the mask, can be created.

In one set of embodiments, a reaction entity or a binding partner may be immobilized relative to all of the nanoscale wire, or to only a portion of the nanoscale wire, for example, immobilized relative to a second portion of the nanoscale wire. In some cases, more than one type of reaction entity and/or binding partner may immobilized to a second portion of a nanoscale wire, and/or to different portions of the nanoscale wire.

Thus, in some cases, a nanoscale wire may be prepared having a first portion comprising a metal-semiconductor compound, and a second portion that does not include a metal-semiconductor compound. Immobilized relative to the second portion (or "channel") of the nanoscale wire may be one or more binding partners, e.g., directly attached or indirectly attached, for instance, via a linker, as described above. Minimizing the size of the second portion of the nanoscale wire, relative to the first portion of the nanoscale wire, in some cases, may facilitate determination of an analyte (for example, its kinetics or other dynamical information), such as a nucleic acid, for instance, due to the small area of the second portion and the relatively few numbers of binding partners that are immobilized relative thereto. In some cases, binding events to other portions of a nanoscale wire (e.g., other portions of a nanoscale wire having binding partners) may not affect changes (or may affect to a lesser or insubstantial degree) in electrical properties of those other portions (as an example, in a nanoscale wire having metal-semiconductor compounds, those portions of the metal-semiconductor compound may be metallic, and binding of an analyte to binding partners immobilized relative to those portions of the nanoscale wire may not significantly alter the electrical properties of the nanoscale wire). Also, by minimizing the sizes of the contacts to the second portion of the nanoscale wire and/or the electrostatic field effect from them, the signal due to binding of the analyte to the nanoscale wire may be enhanced. Thus, for instance, due to the small number of binding partners bound to the second portion of the nanoscale wire and/or enhanced signal from the analyte, the binding of even a single molecule (or a small number of molecules) of analyte to one of the binding partners may be detected, e.g., as a change in an electrical property (e.g., resistance or conductivity) of the nanoscale wire. See also Example 5 for an illustration of this sensitivity. Thus, in some cases, single binding events of an analyte, such as a nucleic acid, to a nanoscale wire may be determined, and in some cases, the identity of similar analytes may be determined, e.g., through differences in binding characteristics, e.g., through determination of binding constants, rates of association and/or dissociation, etc.

In addition, in some cases, such as with nucleic acids such as DNA, a charged analyte bound to a binding partner immobilized relative to a nanowire may "expel" or prevent other charged analytes from binding to nearby binding partners. This "charge separation" effect may be determined, for instance, by determining the "Debye screening length." As known to those of ordinary skill in the art, the Debye screening length can vary for a particular analyte in a particular solution, e.g., due to the presence of other ions in solution. As an example, for DNA, the Debye screening length in a typical buffer solution may be between 30 nm and 100 nm. Due to the screening effect, only a small number of analytes can bind to a nanoscale wire, and in certain cases, e.g., if the portion of the nanoscale wire having binding partners is sufficiently small, e.g., of the same order of magnitude as the Debye screening length, or even smaller, then only a single analyte molecule (e.g., one nucleic acid molecule) may be able to become immobilized relative to the nanoscale wire. Thus, in one embodiment, a solution may comprise an analyte and a nanoscale wire comprising a portion having immobilized relative thereto a binding partner to the analyte, where the Debye screening length of the analyte is greater than the greatest dimension of the portion of the nanoscale wire having the binding partner.

Some aspects of the invention may utilize various techniques to fabricate or synthesize individual nanoscale wires. For example, in some embodiments, metal-catalyzed CVD techniques ("chemical vapor deposition") may be used to synthesize individual nanoscale wires. CVD synthetic procedures useful for preparing individual wires directly on surfaces and in bulk form are generally known, and can readily be carried out by those of ordinary skill in the art.

One technique that may be used to grow nanoscale wires is catalytic chemical vapor deposition ("C-CVD"). In the C-CVD method, the reactant molecules are formed from the vapor phase, as opposed to from laser vaporization. In C-CVD, nanoscale wires may be doped by introducing the doping element into the vapor phase reactant (e. g. diborane and phosphane for p-type and n-type doped regions). The doping concentration may be controlled by controlling the relative amount of the doping compound introduced in the composite target.

Nanoscopic wires may also be grown through laser catalytic growth. See, for example, Morales, et al., "A Laser Ablation Method for the Synthesis of Crystalline Semiconductor Nanowires," *Science,* 279:208-211 (1998). In laser catalytic growth, dopants may be controllably introduced during vapor phase growth of nanoscale wires. Laser vaporization of a composite target composed of a desired material (e. g. silicon or indium phosphide) and a catalytic material (e. g. a nanoparticle catalyst) can create a hot, dense vapor. The vapor condenses into liquid nanoclusters through collision with a buffer gas. Growth may begin when the liquid nanoclusters become supersaturated with the desired phase and can continue as long as reactant is available. Growth may terminate when the nanoscale wire passes out of the hot reaction zone or when the temperature is decreased. The nanoscale wire may be further subjected to different semiconductor reagents during growth. If uniform diameter nanoclusters (e.g., less than 10-20% variation depending on how uniform the nanoclusters are) are used as the catalytic cluster, nanoscale wires with uniform size (diameter) distribution can be produced, where the diameter of the nanoscale wires is determined by the size of the catalytic clusters.

Other techniques to produce nanoscale semiconductors such as nanoscale wires are also within the scope of the present invention. For example, nanoscale wires of any of a variety of materials may be grown directly from vapor phase through a vapor-solid process. Also, nanoscale wires may also be produced by deposition on the edge of surface steps, or other types of patterned surfaces. Further, nanoscale wires may be grown by vapor deposition in or on any generally elongated template. The porous membrane may be porous silicon, anodic alumina, a diblock copolymer, or any other similar structure. The natural fiber may be DNA molecules, protein molecules carbon nanotubes, or any other elongated structures. For the above described techniques, the source materials may be a solution or a vapor.

In some cases, the nanoscale wire may be doped after formation. In one technique of post-synthetic doping of nanoscale wires, a nanoscale wire having a substantially homogeneous composition is first synthesized, then is doped post-synthetically with various dopants. Such doping may occur throughout the entire nanoscale wire, or in one or more portions of the nanoscale wire, for example, in a wire having multiple regions differing in composition. Thus, as a specific non-limiting example, a semiconductor nanoscale wire may be prepared, then one or more regions of the nanoscale wire may be exposed to a dopant, thus resulting in a semiconductor nanoscale wire having a series of undoped semiconductor regions and doped semiconductor regions.

In one set of embodiments, the invention includes a nanoscale wire (or other nanostructured material) that is a single crystal. As used herein, a "single crystal" item (e.g., a semiconductor) is an item that has covalent bonding, ionic bonding, or a combination thereof throughout the item. Such a single-crystal item may include defects in the crystal, but is to be distinguished from an item that includes one or more crystals, not ionically or covalently bonded, but merely in close proximity to one another.

Various embodiments of the invention include the assembly, or controlled placement, of nanoscale wires on a surface. Any substrate may be used for nanoscale wire placement, for example, a substrate comprising a semiconductor, a substrate comprising a metal, a substrate comprising a glass, a substrate comprising a polymer, a substrate comprising a gel, a substrate that is a thin film, a substantially transparent substrate, a non-planar substrate, a flexible substrate, a curved substrate, etc. In some cases, assembly can be carried out by aligning nanoscale wires using an electrical field. In other cases, assembly can be performed using an arrangement involving positioning a fluid flow directing apparatus to direct fluid containing suspended nanoscale wires toward and in the direction of alignment with locations at which nanoscale wires are desirably positioned.

In certain cases, a nanoscale wire (or other nanostructure) is formed on the surface of a substrate, and/or is defined by a feature on a substrate. In one example, a nanostructure, such as a nanoscale wire, is formed as follows. A substrate is imprinted using a stamp or other applicator to define a pattern, such as a nanoscale wire or other nanoscale structure. After removal of the stamp or other applicator, at least a portion of the imprintable layer is removed, for example, through etching processes such as reactive ion etching (RIE), or other known techniques. In some cases, enough imprintable material may be removed from the substrate so as to expose portions of the substrate free of the imprintable material. A metal or other materials may then be deposited onto at least a portion of the substrate, for example, gold, copper, silver, chromium, etc. In some cases, a "lift-off" step may then be performed, where at least a portion of the imprintable material is removed from the substrate. Metal or other material deposited onto the imprintable material may be removed along with the removal of the imprintable material, for example, to form one or more nanoscale wires. Structures deposited on the surface may be connected to one or more electrodes in some cases. The substrate may be any suitable substrate that can support an imprintable layer, for example, comprising a semiconductor, a metal, a glass, a polymer, a gel, etc. In some cases, the substrate may be a thin film, substantially transparent, non-planar, flexible, and/or curved, etc.

In certain cases, an array of nanoscale wires may be produced by providing a surface having a plurality of substantially aligned nanoscale wires, and removing, from the surface, a portion of one or more of the plurality of nanoscale wires. The remaining nanoscale wires on the surface may then be connected to one or more electrodes. In certain cases, the nanoscopic wires are arranged such that they are in contact with each other; in other instances, however, the aligned nanoscopic wires may be at a pitch such that they are substantially not in physical contact.

In certain cases, nanoscale wires are positioned proximate a surface using flow techniques, i.e., techniques where one or more nanoscale wires may be carried by a fluid to a substrate. Nanoscale wires (or any other elongated structures) can be aligned by inducing a flow of a nanoscale wire solution on surface, where the flow can include channel flow or flow by any other suitable technique. Nanoscale wire arrays with controlled position and periodicity can be produced by patterning a surface of a substrate and/or conditioning the surface of the nanoscale wires with different functionalities, where the position and periodicity control may be achieved by designing specific complementary forces between the patterned surface and the nanoscale wires. Nanoscale wires can also be assembled using a Langmuir-Blodgett (LB) trough. Nanoscale wires may first be surface-conditioned and dispersed to the surface of a liquid phase to form a Langmuir-Blodgett film. In some cases, the liquid may include a surfactant, which can, in some cases, reduce aggregation of the nanoscale wires and/or reduce the ability of the nanoscale wires to interact with each other. The nanoscale wires can be aligned into different patterns (such as parallel arrays or fibers) by compressing the surface or reducing the surface area of the surface.

Another arrangement involves forming surfaces on a substrate including regions that selectively attract nanoscale wires surrounded by regions that do not selectively attract them. Surfaces can be patterned using known techniques such as electron-beam patterning, "soft-lithography" such as that described in International Patent Application Serial No. PCT/US96/03073, entitled "Microcontact Printing on Surfaces and Derivative Articles," filed Mar. 1, 1996, published as Publication No. WO 96/29629 on Jul. 26, 1996; or U.S. Pat. No. 5,512,131, entitled "Formation of Microstamped Patterns on Surfaces and Derivative Articles," issued Apr. 30, 1996, each of which is incorporated herein by reference. Additional techniques are described in U.S. Patent Application Ser. No. 60/142,216, entitled "Molecular Wire-Based Devices and Methods of Their Manufacture," filed Jul. 2, 1999, incorporated herein by reference. Fluid flow channels can be created at a size scale advantageous for placement of nanoscale wires on surfaces using a variety of techniques such as those described in International Patent Application Serial No. PCT/US97/04005, entitled "Method of Forming Articles and Patterning Surfaces via Capillary Micromolding," filed Mar. 14, 1997, published as Publication No. WO 97/33737 on Sep. 18, 1997, and incorporated herein by reference. Other techniques include those described in U.S. Pat. No. 6,645,432, entitled "Microfluidic Systems Including Three-dimensionally Arrayed Channel Networks," issued Nov. 11, 2003, incorporated herein by reference.

Chemically patterned surfaces other than SAM-derivatized surfaces can be used, and many techniques for chemically patterning surfaces are known. Another example of a chemically patterned surface may be a micro-phase separated block copolymer structure. These structures may provide a stack of dense lamellar phases, where a cut through these phases reveals a series of "lanes" wherein each lane represents a single layer. The assembly of nanoscale wires onto substrate and electrodes can also be assisted using bimolecular recognition in some cases. For example, one biological binding partner may be immobilized onto the nanoscale wire surface and the other one onto a substrate or an electrode using physical adsorption or covalently linking. An example technique which may be used to direct the assembly of a nanoscopic wires on a substrate is by using "SAMs," or selfassembled monolayers. Any of a variety of substrates and SAM-forming material can be used along with microcontact printing techniques, such as those described in International Patent Application Serial No. PCT/US96/03073, entitled "Microcontact Printing on Surfaces and Derivative Articles," filed Mar. 1, 1996, published as Publication No. WO 96/29629 on Jul. 26, 1996, incorporated herein by reference in its entirety.

In some cases, the nanoscale wire arrays may also be transferred to another substrate, e.g., by using stamping techniques. In certain instances, nanoscale wires may be assembled using complementary interaction, i.e., where one or more complementary chemical, biological, electrostatic, magnetic or optical interactions are used to position one or more nanoscale wires on a substrate. In certain cases, physical patterns may be used to position nanoscale wires proximate a surface. For example, nanoscale wires may be positioned on a substrate using physical patterns, for instance, aligning the nanoscale wires using corner of the surface steps or along trenches on the substrate.

In another set of embodiments, the nanoscale wires may be transferred to a substrate by contacting at least some of the nanoscale wires with the second substrate, e.g., by moving or "sliding" the substrates relative to each other, in some cases causing alignment of the nanoscale wires on the second substrate. For instance, in one embodiment, a first substrate, having a plurality of nanoscale wires thereon, is brought into contact with a second substrate to transfer one or more nanoscale wires from one to the other. The first substrate can then be moved or slid against a second substrate (and/or the second substrate is moved against the first substrate) such that at least some of the nanoscale wires are transferred from the first substrate to the second substrate. The nanoscale wires can become immobilized relative to the second substrate through ionic interactions, hydrophobic interactions, van der Waals interactions, etc., or the like. Further details, as well as additional methods of nanoscale wire transfer useful in the present invention, are discussed in U.S. Provisional Patent Application Ser. No. 60/790,322, filed Apr. 7, 2006, entitled "Nanoscale Wire Methods and Devices," by Lieber, et al., incorporated herein by reference.

The present invention finds use in a wide range of applications. For instance, in some aspects, any of the techniques described herein may be used in the determination of viruses, cells, or the like, e.g., as in an assay, for example, to detect or diagnose cancer or other medical conditions, toxins or other environmental agents, viruses, or the like. As a specific, non-limiting example, specific DNA or RNA may be identified from a virus under study, while the number of mismatches with a known binding Partner may be indicative of the viral strain of the virus. As another example, mutations within a nucleic acid (e.g., within DNA or RNA) may be determined using various systems and methods of the invention, as previously described, for instance, if the sequence of the binding partner to the nucleic acid is known, the degree of mutation may be indicated by the number of mismatches present. The nucleic acid sample may be taken, for example, from a subject such as a human. In yet another example, a property of an analyte may be determined by allowing the analyte to interact with a binding partner, and the interaction may be analyzed or determined in some fashion, e.g., quantified. In some cases, the degree or amount of interaction (e.g., a binding constant) may be determined, for example, by measuring a property of the nanoscale wire (e.g., an electronic property, such as the conductance) after exposing the nanoscale wire and/or the binding partner to the analyte.

Another set of embodiments is generally directed to an array, such as a microarray, of sensing regions. In some cases, at least some of the sensing regions each comprise one, or a plurality of, nanoscale wires that are individually addressable. In certain instances, at least some of the nanoscale wires comprise binding partners and/or reaction entities, such as those previously described. For example, in one embodiment, some or all of the nanoscale wires may have different binding partners immobilized relative thereto, and optionally, each nanoscale wire may be independently addressable and/or determinable, such that a plurality of different analytes may be detected, for example, a plurality of different nucleic acids (which can be, in some cases, nucleic acids that are similar except for a small number of mismatches as previously described, e.g., SNPs). Thus, the array may be used, for instance, to categorize an individual as a particular genetic type.

As a non-limiting example, DNA from a subject sample may be exposed to an array of nanoscale wires having binding partners to nucleic acid regions where SNPs often occur (e.g., nucleic acids that are complementary to those regions), and the presence of SNP alleles in the DNA may be determined, i.e., whether certain portions of the DNA bind to binding partners on the array of nanoscale wires, and/or with what degree of binding. For instance, DNA from a first subject having a first SNP allele such as a "wild-type" SNP allele may be perfectly complementary to a nucleic acid binding partner immobilized relative to a nanoscale wire on the array, while DNA from a second subject may exhibit one or more mismatches to the nucleic acid binding partner, which mismatches can be detected, e.g., as described herein.

In some embodiments, the invention includes a microarray including a plurality of sensing regions, at least some of which comprise one or more nanoscale wires. The microarray, including some or all of the sensing regions, may define a sensing element in a sensor device. At least some of the nanoscale wires are able to determine an analyte suspected to be present in a sample that the sensing region of the microarray is exposed to, for example, the nanoscale wire may comprise a reaction entity able to interact with an analyte. If more than one nanoscale wire is present within the sensing region, the nanoscale wires may be able to detect the same analyte and/or different analytes, depending on the application. For example, the nanoscale wires within the sensing region of the microarray may be able to determine 1, 2, 3, 4, 5, 6, 8, 10, 12, 14, 16, 18, 20, 22, 24, 26, 28, 30, 40, 50, or more analytes or types of analytes. As an example, a microarray may have one or more sensing regions, at least some of which comprise nanoscale wires having nucleic acids immobilized with respect to the nanoscale wires, e.g., as described herein. The microarray may be used to determine analytes in one, or a number of samples. For example, the microarray may include at least 2, at least 3, at least 5, at least 10, at least 15, at least 20, at least 25, at least 30, at least 50, at least 70, at least 100, at least 200, at least 300, at least 500, at least 1,000, at least 3,000, at least 5,000, or at least 10,000 or more sensing regions, at least some of which may be used to determine the analyte of a sample placed on the sensing region. In certain cases, the microarray may have a high density of nanoscale wires, at least some of which may be to individually addressable, and at least some of which can be used to determine an analyte suspected to be present in a sample. For instance, the density of nanoscale wires may be at least about 100 nanoscale wires/cm$^2$, and in some cases, at least about 110 nanoscale wires/cm$^2$, at least about 120 nanoscale wires/cm$^2$, at least about 130 nanoscale wires/cm$^2$, at least about 150 nanoscale wires/cm$^2$, at least about 200 nanoscale wires/cm$^2$, at least about 250 nanoscale wires/cm$^2$, or at least about 500 nanoscale wires/cm$^2$.

An example of a sensing region is shown in FIG. 6A. In this figure, the sensing region 220 includes a first electrode 221 and a second or counter electrode 222. The first electrode is generally elongated (i.e., one dimension of the electrode is significantly longer in one dimension than another). One or more nanoscale wires 227 are in electrical communication with first electrode 221 and second electrode 222, and at least some of the nanoscale wires may comprise a reaction entity able to interact with an analyte. First electrode 221 is in electronic communication with an electrical contact or lead 225 through electronic connection 223 (e.g., a wire or an etched electronic pathway), while second electrode 222 is in electronic communication with an electrical contact 225 through electronic connection 224. Analyte 229 is present in a sample that is placed within sensing region 220, and is able to interact with a reaction entity present on a nanoscale wire 227 (e.g., by binding, for example, covalently). Upon such an interaction, an electrical property of the nanoscale wire, e.g., conductivity, is altered (e.g., through a charge interaction between the analyte and the nanoscale wire), which can be determined by determining a change in conductivity of the nanoscale wire, for instance, by measuring a change in conductivity between electrical contact 225 and electrical contact 226.

Additional nanoscale wires may be added to the sensing region. For example, in FIG. 6B, sensing region 220 has five second or counter electrodes 222. At least some of nanoscale wires 211, 212, 213, 214 connect at least some of the second electrodes 222 with first electrode 221, and at least some of the nanoscale wires may comprise a reaction entity able to interact with an analyte. For instance, nanoscale wires 211 may interact with a first analyte, but not with a second analyte or a third analyte, while nanoscale wires 212 may interact with only the second analyte and nanoscale wires 213 may interact with only the third analyte. Upon a binding event of an analyte with a corresponding reaction entity, a property of the nanoscale wire, such as conductance, may change, and may be determined, as previously described.

Additional arrays and microarrays useful in various embodiments of the invention are discussed in U.S. Provisional Patent Application Ser. No. 60/707,136, filed Aug. 9, 2005, entitled "Nanoscale Sensors," by Lieber, et al., incorporated herein by reference.

In one aspect, the present invention provides any of the above-mentioned devices packaged in kits, optionally including instructions for use of the devices. As used herein, "instructions" can define a component of instructional utility (e.g., directions, guides, warnings, labels, notes, FAQs ("frequently asked questions"), etc., and typically involve written instructions on or associated with packaging of the invention. Instructions can also include instructional communications in any form (e.g., oral, electronic, digital, optical, visual, etc.), provided in any manner such that a user will clearly recognize that the instructions are to be associated with the device, e.g., as discussed herein. Additionally, the kit may include other components depending on the specific application, for example, containers, adapters, syringes, needles, replacement parts, etc.

In some embodiments, one or more of the nanoscale wires described herein, and/or one or more of the devices or methods described herein, may be promoted. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, replacing, or the like that can be associated with the methods and compositions of the invention, e.g., as discussed herein. Promoting may also include, in some cases, seeking approval from a government agency to sell a composition of the invention for medicinal purposes. Methods of promotion can be performed by any party including, but not limited to, businesses (public or private), contractual or sub-contractual agencies, educational institutions such as colleges and universities, research institutions, hospitals or other clinical institutions, governmental agencies, etc. Promotional activities may include instructions or communications of any form (e.g., written, oral, and/or electronic communications, such as, but not limited to, e-mail, telephonic, facsimile, Internet, Web-based, etc.) that are clearly associated with the invention.

The following definitions will aid in the understanding of the invention. Interspersed with these definitions is additional disclosure of various aspects of the invention.

Certain devices of the invention may include wires or other components of scale commensurate with nanometer-scale wires, which includes nanotubes and nanowires. In some embodiments, however, the invention comprises articles that may be greater than nanometer size (e. g., micrometer-sized). As used herein, "nanoscopic-scale," "nanoscopic," "nanometer-scale," "nanoscale," the "nano-" prefix (for example, as in "nanostructured"), and the like generally refers to elements or articles having widths or diameters of less than about 1 micron, and less than about 100 nm in some cases. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater).

As used herein, an "elongated" article (e.g. a semiconductor or a section thereof) is an article for which, at any point along the longitudinal axis of the article, the ratio of the length of the article to the largest width at that point is greater than 2:1.

A "width" of an article, as used herein, is the distance of a straight line from a point on a perimeter of the article, through the center of the article, to another point on the perimeter of the article. As used herein, a "width" or a "cross-sectional dimension" at a point along a longitudinal axis of an article is the distance along a straight line that passes through the center of a cross-section of the article at that point and connects two points on the perimeter of the cross-section. The "cross-section" at a point along the longitudinal axis of an article is a plane at that point that crosses the article and is orthogonal to the longitudinal axis of the article. The "longitudinal axis" of an article is the axis along the largest dimension of the article. Similarly, a "longitudinal section" of an article is a portion of the article along the longitudinal axis of the article that can have any length greater than zero and less than or equal to the length of the article. Additionally, the "length" of an elongated article is a distance along the longitudinal axis from end to end of the article.

As used herein, a "cylindrical" article is an article having an exterior shaped like a cylinder, but does not define or reflect any properties regarding the interior of the article. In other words, a cylindrical article may have a solid interior, may have a hollowed-out interior, etc. Generally, a cross-section of a cylindrical article appears to be circular or approximately circular, but other cross-sectional shapes are also possible, such as a hexagonal shape. The cross-section may have any arbitrary shape, including, but not limited to, square, rectangular, or elliptical. Regular and irregular shapes are also included.

As used herein, an "array" of articles (e.g., nanoscopic wires) comprises a plurality of the articles, for example, a series of aligned nanoscale wires, which may or may not be in contact with each other. As used herein, a "crossed array" or a "crossbar array" is an array where at least one of the articles contacts either another of the articles or a signal node (e.g., an electrode).

As used herein, a "wire" generally refers to any material having a conductivity of or of similar magnitude to any semiconductor or any metal, and in some embodiments may be used to connect two electronic components such that they are in electronic communication with each other. For example, the terms "electrically conductive" or a "conductor" or an "electrical conductor" when used with reference to a "conducting" wire or a nanoscale wire, refers to the ability of that wire to pass charge. Typically, an electrically conductive nanoscale wire will have a resistivity comparable to that of metal or semiconductor materials, and in some cases, the electrically conductive nanoscale wire may have lower resistivities, for example, resistivities of less than about 100 microOhm cm ($\mu\Omega$ cm). In some cases, the electrically conductive nanoscale wire will have a resistivity lower than about $10^{-3}$ ohm meters, lower than about $10^{-4}$ ohm meters, or lower than about $10^{-6}$ ohm meters or $10^{-7}$ ohm meters.

A "semiconductor," as used herein, is given its ordinary meaning in the art, i.e., an element having semiconductive or semi-metallic properties (i.e., between metallic and non-metallic properties). An example of a semiconductor is silicon. Other non-limiting examples include gallium, germanium, diamond (carbon), tin, selenium, tellurium, boron, or phosphorus.

A "nanoscopic wire" (also known herein as a "nanoscopic-scale wire" or "nanoscale wire") generally is a wire, that at any point along its length, has at least one cross-sectional dimension and, in some embodiments, two orthogonal cross-sectional dimensions less than 1 micron, less than about 500 nm, less than about 200 nm, less than about 150 nm, less than about 100 nm, less than about 70, less than about 50 nm, less than about 20 nm, less than about 10 nm, or less than about 5 nm. In other embodiments, the cross-sectional dimension can be less than 2 nm or 1 nm. In one set of embodiments, the nanoscale wire has at least one cross-sectional dimension ranging from 0.5 nm to 100 nm or 200 nm. In some cases, the nanoscale wire is electrically conductive. Where nanoscale wires are described having, for example, a core and an outer region, the above dimensions generally relate to those of the core. The cross-section of a nanoscopic wire may be of any arbitrary shape, including, but not limited to, circular, square, rectangular, annular, polygonal, or elliptical, and may be a regular or an irregular shape. The nanoscale wire may be solid or hollow. A non-limiting list of examples of materials from which nanoscale wires of the invention can be made appears below. Any nanoscale wire can be used in any of the embodiments described herein, including carbon nanotubes, molecular wires (i.e., wires formed of a single molecule), nanorods, nanowires, nanowhiskers, organic or inorganic conductive or semiconducting polymers, and the like, unless otherwise specified. Other conductive or semiconducting elements that may not be molecular wires, but are of various small nanoscopic-scale dimensions, can also be used in some instances, e.g. inorganic structures such as main group and metal atom-based wire-like silicon, transition metal-containing wires, gallium arsenide, gallium nitride, indium phosphide, germanium, cadmium selenide, etc. A wide variety of these and other nanoscale wires can be grown on and/or applied to surfaces in patterns useful for electronic devices in a manner similar to techniques described herein involving the specific nanoscale wires used as examples, without undue experimentation. The nanoscale wires, in some cases, may be formed having dimensions of at least about 1 micron, at least about 3 microns, at least about 5 microns, or at least about 10 microns or about 20 microns in length, and can be less than about 100 nm, less than about 80 nm, less than about 60 nm, less than about 40 nm, less than about 20 nm, less than about 10 nm, or less than about 5 nm in thickness (height and width). The nanoscale wires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

A "nanowire" (e. g. comprising silicon and/or another semiconductor material, such as an elemental semiconductor) is a nanoscopic wire that is typically a solid wire, and may be elongated in some cases. Preferably, a nanowire (which is abbreviated herein as "NW") is an elongated semiconductor, i.e., a nanoscale semiconductor. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used.

As used herein, a "nanotube" (e.g. a carbon nanotube) is a nanoscopic wire that is hollow, or that has a hollowed-out core, including those nanotubes known to those of ordinary skill in the art. "Nanotube" is abbreviated herein as "NT." Nanotubes are used as one example of small wires for use in the invention and, in certain embodiments, devices of the invention include wires of scale commensurate with nanotubes. Examples of nanotubes that may be used in the present invention include, but are not limited to, single-walled nanotubes (SWNTs). Structurally, SWNTs are formed of a single graphene sheet rolled into a seamless tube. Depending on the diameter and helicity, SWNTs can behave as one-dimensional metals and/or semiconductors. SWNTs. Methods of manufacture of nanotubes, including SWNTs, and characterization are known. Methods of selective functionalization on the ends and/or sides of nanotubes also are known, and the present invention makes use of these capabilities for molecular electronics in certain embodiments. Multi-walled nanotubes are well known, and can be used as well.

Examples of nanotubes that may be used in the present invention include single-walled nanotubes (SWNTs) that exhibit unique electronic and/or chemical properties that are particularly suitable for molecular electronics. Structurally, SWNTs are formed of a single graphene sheet rolled into a seamless tube with a diameter on the order of about 0.5 nm to about 5 nm and a length that can exceed about 10 microns. Depending on diameter and helicity, SWNTs can behave as one-dimensional metals or semiconductor and are currently available as a mixture of metallic and semiconducting nanotubes. Methods of manufacture of nanotubes, including SWNTs, and characterization are known. Methods of selective functionalization on the ends and/or sides of nanotubes also are known, and the present invention makes use of these capabilities for molecular electronics. The basic structural/electronic properties of nanotubes can be used to create connections or input/output signals, and nanotubes have a size consistent with molecular scale architecture. Those of ordinary skill in the art will know of methods of preparing nanotubes. See, for example, Kong, et al., "Synthesis of Individual Single-Walled Carbon Nanotubes on Patterned Silicon Wafers," *Nature,* 395:878-881 (1998); or Kong, et al., "Chemical Vapor Deposition of Methane for Single-Walled Carbon Nanotubes," *Chem. Phys. Lett.,* 292:567-574 (1998).

Certain nanoscale wires of the present invention are individual nanoscale wires. As used herein, "individual nanoscale wires" means a nanoscale wire free of contact with another nanoscale wire (but not excluding contact of a type that may be desired between individual nanoscale wires in a crossbar array). For example, an "individual" or a "free-standing" article may, at some point in its life, not be attached to another article, for example, with another nanoscopic wire, or the free-standing article may be in solution. Such a free-standing article may be, for instance, removed from the location where it is made, as an individual article, and transported to a different location and combined with different components to make a functional device such as those described herein and those that would be contemplated by those of ordinary skill in the art upon reading this disclosure. This is in contrast to conductive portions of articles which differ from surrounding material only by having been altered chemically or physically, in situ, i.e., where a portion of a uniform article is made different from its surroundings by selective doping, etching, etc.

In some cases, the nanoscale wire may comprise inorganic structures such as Group IV, Group III/Group V, Group II/Group VI elements, transition group elements, or the like, as described herein. For example, the nanoscale wires may be made of semiconducting materials such as silicon, indium phosphide, gallium nitride and others. The nanoscale wires may also include, for example, any organic, inorganic molecules that are polarizable or have multiple charge states. For example, nanoscopic-scale structures may include main group and metal atom-based wire-like silicon, transition metal-containing wires, gallium arsenide, gallium nitride, indium phosphide, germanium, or cadmium selenide structures. In one set of embodiments, the nanoscale wire includes a metal-semiconductor compound.

The nanoscale wires may include various combinations of materials, including semiconductors and dopants. The following are non-comprehensive examples of materials that may be used as dopants. For example, the dopant and/or the nanoscale wire may be an elemental semiconductor, for example, silicon, germanium, tin, selenium, tellurium, boron, diamond, or phosphorus. The dopant may also be a solid solution of various elemental semiconductors. Examples include a mixture of boron and carbon, a mixture of boron and P(BP$_6$), a mixture of boron and silicon, a mixture of silicon and carbon, a mixture of silicon and germanium, a mixture of silicon and tin, or a mixture of germanium and tin.

In some embodiments, the dopant and/or the semiconductor may include mixtures of Group IV elements, for example, a mixture of silicon and carbon, or a mixture of silicon and germanium. In other embodiments, the dopant or the semiconductor may include a mixture of a Group III and a Group V element, for example, BN, BP, BAs, AlN, AlP, AlAs, AlSb, GaN, GaP, GaAs, GaSb, InN, InP, InAs, or InSb. Mixtures of these may also be used, for example, a mixture of BN/BP/BAs, or BN/AlP. In other embodiments, the dopants may include alloys of Group III and Group V elements. For example, the alloys may include a mixture of AlGaN, GaPAs, InPAs, GaInN, AlGaInN, GaInAsP, or the like. In other embodiments, the dopants may also include a mixture of Group II and Group VI semiconductors. For example, the semiconductor may include ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, for example, (ZnCd)Se, or Zn(SSe), or the like. Additionally, alloys of different groups of semiconductors may also be possible, for example, a combination of a Group II-Group VI and a Group III-Group V semiconductor, for example, (GaAs)$_x$(ZnS)$_{1-x}$. Other examples of dopants may include combinations of Group IV and Group VI elements, such as GeS, GeSe, GeTe, SnS, SnSe, SnTe, PbO, PbS, PbSe, or PbTe. Other semiconductor mixtures may include a combination of a Group I and a Group VII, such as CuF, CuCl, CuBr, CuI, AgF, AgCl, AgBr, AgI, or the like. Other dopant compounds may include different mixtures of these elements, such as BeSiN$_2$, CaCN$_2$, ZnGeP$_2$, CdSnAs$_2$, ZnSnSb$_2$, CuGeP$_3$, CuSi$_2$P$_3$, Si$_3$N$_4$, Ge$_3$N$_4$, Al$_2$O$_3$, (Al,Ga,In)$_2$(S,Se, Te)$_3$, Al$_2$CO, (Cu,Ag)(Al,Ga,In,Tl,Fe)(S,Se,Te)$_2$ and the like.

For Group IV dopant materials, a p-type dopant may be selected from Group III, and an n-type dopant may be selected from Group V, for example. For silicon semiconductor materials, a p-type &pant may be selected from the group consisting of B, Al and In, and an n-type dopant may be selected from the group consisting of P, As and Sb. For Group III-Group V semiconductor materials, a p-type dopant may be selected from Group II, including Mg, Zn, Cd and Hg, or Group IV, including C and Si. An n-type dopant may be selected from the group consisting of Si, Ge, Sn, S, Se and Te. It will be understood that the invention is not limited to these dopants, but may include other elements, alloys, or materials as well.

As used herein, the term "Group," with reference to the Periodic Table, is given its usual definition as understood by one of ordinary skill in the art. For instance, the Group II elements include Mg and Ca, as well as the Group II transition elements, such as Zn, Cd, and Hg. Similarly, the Group III elements include B, Al, Ga, In and Tl; the Group IV elements include C, Si, Ge, Sn, and Pb; the Group V elements include N, P, As, Sb and Bi; and the Group VI elements include O, S, Se, Te and Po. Combinations involving more than one element from each Group are also possible. For example, a Group II-VI material may include at least one element from Group II and at least one element from Group VI, e.g., ZnS, ZnSe, ZnSSe, ZnCdS, CdS, or CdSe. Similarly, a Group III-V material may include at least one element from Group III and at least one element from Group V, for example GaAs, GaP, GaAsP, InAs, InP, AlGaAs, or InAsP. Other dopants may also be included with these materials and combinations thereof, for example, transition metals such as Fe, Co, Te, Au, and the like. The nanoscale wire of the present invention may further include, in some cases, any organic or inorganic molecules. In some cases, the organic or inorganic molecules are polarizable and/or have multiple charge states.

As used herein, transition metal groups of the periodic table, when referred to in isolation (i.e., without referring to the main group elements), are indicated with a "B." The transition metals elements include the Group IB elements (Cu, Ag, Au), the Group IIB elements (Zn, Cd, Hg), the Group IIIB elements (Sc, Y, lanthanides, actinides), the Group IVB elements (Ti, Zr, Hf), the Group VB elements (V, Nb, Ta), the Group VIB elements (Cr, Mo, W), the Group VIIB elements (Mn, Tc, Re), and the Group VIIIB elements (Fe, Co, Ni, Ru, Rh, Pd, Os, Ir, Pt).

In some embodiments, at least a portion of a nanoscopic wire may be a bulk-doped semiconductor. As used herein, a "bulk-doped" article (e. g. an article, or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles such as carbon nanotubes are typically doped after the base material is grown, and thus the dopant only extends a finite distance from the surface or exterior into the interior of the crystalline lattice. It should be understood that "bulk-doped" does not define or reflect a concentration or amount of doping in a semiconductor, nor does it necessarily indicate that the doping is uniform. In particular, in some embodiments, a bulk-doped semiconductor may comprise two or more bulk-doped regions. Thus, as used herein to describe nanoscopic wires, "doped" refers to bulk-doped nanoscopic wires, and, accordingly, a "doped nanoscopic (or nanoscale) wire" is a bulk-doped nanoscopic wire. "Heavily doped" and "lightly doped" are terms the meanings of which are understood by those of ordinary skill in the art.

A bulk-doped semiconductor may include various combinations of materials, including other semiconductors and dopants. In one set of embodiments, the nanoscale wire may comprise a semiconductor that is doped with an appropriate dopant to create an n-type or p-type semiconductor as desired. For example, silicon may be doped with boron, aluminum, phosphorus, or arsenic. Laser catalytic growth may be used to introduce controllably the dopants during the vapor phase growth of silicon nanoscale wires. Controlled doping of nanoscale wires can be carried out to form, e.g., n-type or p-type semiconductors. Dopants including, but not limited to, zinc, cadmium, or magnesium can be used to form p-type semiconductors, and dopants including, but not limited to, tellurium, sulfur, selenium, or germanium can be used as dopants to form n-type semiconductors. These materials define direct band gap semiconductor materials and these and doped silicon are well known to those of ordinary skill in the art. The present invention contemplates use of any doped silicon or direct band gap semiconductor materials for a variety of uses, as discussed above. Examples of doped semiconductors can be seen in U.S. patent application Ser. No. 09/935,776, filed Aug. 22, 2001, entitled "Doped Elongated Semiconductors, Growing Such Semiconductors, Devices Including Such Semiconductors, and Fabricating Such Devices," by Lieber, et al., published as U.S. Patent Application Publication No. 2002/0130311 on Sep. 19, 2002; or U.S. patent application Ser. No. 10/196,337, filed Jul. 16, 2002, entitled "Nanoscale Wires and Related Devices," by Lieber, et al., published as U.S. Patent Application Publication No. 2003/0089899 on May 15, 2003; each incorporated herein by reference.

The invention provides, as previously described, a nanoscale wire or wires forming part of a system constructed and arranged to determine an analyte in a sample to which the nanoscale wire(s) is exposed.

The term "sample" refers to any cell, tissue, or fluid from a biological source (a "biological sample"), or any other medium, biological or non-biological, that can be evaluated in accordance with the invention including, such as serum or water. The sample may be contained in a fluid, e.g., in solution. A sample includes, but is not limited to, a biological sample drawn from an organism (e.g. a human, a non-human mammal, an invertebrate, a plant, a fungus, an algae, a bacteria, a virus, etc.), a sample drawn from food designed for human consumption, a sample including food designed for animal consumption such as livestock feed, milk, an organ donation sample, a sample of blood destined for a blood supply, a sample from a water supply, or the like.

A "sample suspected of containing" a particular component means a sample with respect to which the content of the component is unknown. "Sample" in this context includes naturally-occurring samples, such as physiological samples from humans or other animals, samples from food, livestock feed, etc. Typical samples taken from humans or other animals include tissue biopsies, cells, whole blood, serum or other blood fractions, urine, ocular fluid, saliva, or fluid or other samples from tonsils, lymph nodes, needle biopsies, etc.

A variety of sample sizes, for exposure of a sample to a nanoscale sensor of the invention, can be used in various embodiments. As examples, the sample size used in nanoscale sensors may be less than or equal to about 10 microliters, less than or equal to about 1 microliter, or less than or equal to about 0.1 microliter. The sample size may be as small as about 10 nanoliters, 1 nanoliter, or less, in certain instances. The nanoscale sensor also allows for unique accessibility to biological species and may be used for in vivo and/or in vitro applications. When used in vivo, in some case, the nanoscale sensor and corresponding method result in a minimally invasive procedure.

"Determine," as used herein, generally refers to the analysis of a state or condition, for example, quantitatively or qualitatively. For example, a species, or an electrical state of a system may be determined. "Determining" may also refer to the analysis of an interaction between two or more species, for example, quantitatively or qualitatively, and/or by detecting the presence or absence of the interaction, e.g. determination of the binding between two species. As an example, an analyte may cause a determinable change in an electrical property of a nanoscale wire (e.g., electrical conductivity, resistivity, impedance, etc.), a change in an optical property of the nanoscale wire, etc. Examples of determination techniques include, but are not limited to, conductance measurement, current measurement, voltage measurement, resistance measurement, piezoelectric measurement, electrochemical measurement, electromagnetic measurement, photodetection, mechanical measurement, acoustic measurement, gravimetric measurement, and the like. "Determining" also means detecting or quantifying interaction between species.

As used herein, the term "reaction entity" refers to any entity that can interact with an analyte in such a manner as to cause a detectable change in a property of a nanoscale wire. The reaction entity may comprise a binding partner to which the analyte binds. The reaction entity, when a binding partner, can comprise a specific binding partner of the analyte. In some cases, the reaction entity can form a coating on the nanoscale wire. Non-limiting examples of reaction entities include a nucleic acid (e.g., DNA or RNA), an antibody, a sugar or a carbohydrate, a protein or an enzyme, a ganglioside or a surfactant, etc., e.g., as discussed herein.

In one set of embodiments, a reaction entity associated with the nanoscale wire is able to interact with an analyte. The reaction entity, as "associated" with or "immobilized" relative to the nanoscale wire, may be positioned in relation to the nanoscale wire (e.g., in close proximity or in contact) such that the analyte can be determined by determining a change in a characteristic or property of the nanoscale wire. Interaction of the analyte with the reaction entity may cause a detectable change or modulation in a property of the nanoscale wire, for example, through electrical coupling with the reaction entity. For example, interaction of an analyte with a reaction entity may be determined by determining a change in an electrical property of the nanoscale wire, for example, voltage, current, conductivity, resistivity, inductance, impedance, electrical change, an electromagnetic change, etc.

As used herein, a component that is "immobilized relative to" another component either is fastened to the other component or is indirectly fastened to the other component, e.g., by being fastened to a third component to which the other component also is fastened. For example, a first entity is immobilized relative to a second entity if a species fastened to the surface of the first entity attaches to an entity, and a species on the surface of the second entity attaches to the same entity, where the entity can be a single entity, a complex entity of multiple species, another particle, etc. In certain embodiments, a component that is immobilized relative to another component is immobilized using bonds that are stable, for example, in solution or suspension. In some embodiments, non-specific binding of a component to another component, where the components may easily separate due to solvent or thermal effects, is not preferred.

As used herein, "fastened to or adapted to be fastened to," as used in the context of a species relative to another species or a species relative to a surface of an article (such as a nanoscale wire), or to a surface of an article relative to another surface, means that the species and/or surfaces are chemically or biochemically linked to or adapted to be linked to, respectively, each other via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a nanoscale wire, a binding species specifically biologically coupled to an antibody which is bound to a protein such as protein A, which is attached to a nanoscale wire, a binding species that forms a part of a molecule, which in turn is specifically biologically bound to a binding partner covalently fastened to a surface of a nanoscale wire, etc. A species also is adapted to be fastened to a surface if a surface carries a particular nucleotide sequence, and the species includes a complementary nucleotide sequence.

"Specifically fastened" or "adapted to be specifically fastened" means a species is chemically or biochemically linked to or adapted to be linked to, respectively, another specimen or to a surface as described above with respect to the definition of "fastened to or adapted to be fastened," but excluding essentially all non-specific binding. "Covalently fastened" means fastened via essentially nothing other than one or more covalent bonds.

As used herein, "attached to," in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "attached" in this context includes multiple chemical linkages, multiple chemical/biological linkages, etc., for example, a binding species such as a peptide synthesized on a polystyrene bead. "Covalently attached" means attached via one or more covalent bonds.

The term "binding" refers to the interaction between a corresponding pair of molecules or surfaces that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, and the like. Specific non-limiting examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, virus/cell surface receptor, etc.

The term "binding partner" refers to a molecule that can undergo binding with a particular molecule. Biological binding partners are examples. For example, Protein A is a binding partner of the biological molecule IgG, and vice versa. Other non-limiting examples include nucleic acid-nucleic acid binding, nucleic acid-protein binding, protein-protein binding, enzyme-substrate binding, receptor-ligand binding, receptor-hormone binding, antibody-antigen binding, etc. Binding partners include specific, semi-specific, and non-specific binding partners as known to those of ordinary skill in the art. For example, Protein A is usually regarded as a "non-specific" or semi-specific binder. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include nucleic acids that specifically bind (hybridize) to their complement, antibodies specifically bind to their antigen, binding pairs such as those described above, and the like. The binding may be by one or more of a variety of mechanisms including, but not limited to ionic interactions, and/or covalent interactions, and/or hydrophobic interactions, and/or van der Waals interactions, etc.

The following documents are incorporated herein by reference in their entirety for all purposes, and include additional description of teachings usable with the present invention: U.S. Provisional Patent Application Ser. No. 60/142,216, filed Jul. 2, 1999, entitled "Molecular Wire-Based Devices and Methods of Their Manufacture," by Lieber, et al.; International Patent Application No. PCT/US00/18138, filed Jun. 30, 2000, entitled "Nanoscopic Wire-Based Devices, Arrays, and Methods of Their Manufacture," by Lieber, et al., published as WO 01/03208 on Jan. 11, 2001; U.S. Provisional Patent Application Ser. No. 60/226,835, filed Aug. 22, 2000, entitled "Semiconductor Nanowires," by Lieber, et al.; U.S. Provisional Patent Application Ser. No. 60/254,745, filed Dec. 11, 2000, entitled "Nanowire and Nanotube Nanosensors," by Lieber, et al.; U.S. Provisional Patent Application Ser. No. 60/291,896, filed May 18, 2001, entitled "Nanowire Devices Including Emissive Elements and Sensors," by Lieber, et al.; U.S. Provisional Patent Application Ser. No. 60/292,035, filed May 18, 2001, entitled "Nanowire and Nanotube Sensors," by Lieber, et al.; U.S. Provisional Patent Application Ser. No. 60/292,045, filed May 18, 2001, entitled "Nanowire Electronic Devices Including Memory and Switching Devices," by Lieber, et al.; U.S. Provisional Patent Application Ser. No. 60/292,121, filed May 18, 2001, entitled "Semiconductor Nanowires," by Lieber, et al.; U.S. patent application Ser. No. 09/935,776, filed Aug. 22, 2001, entitled "Doped Elongated Semiconductors, Growing Such Semiconductors, Devices Including Such Semiconductors, and Fabricating Such Devices," by Lieber, et al., published as U.S. Patent Application Publication No. 2002/0130311 on Sep. 19, 2002; International Patent Application No. PCT/US01/26298, filed Aug. 22, 2001, entitled "Doped Elongated Semiconductors, Growing Such Semiconductors, Devices Including Such Semiconductors, and Fabricating Such Devices," by Lieber, et al., published as WO 02/17362 on Feb. 28, 2002; U.S. patent application Ser. No. 10/033,369, filed Oct. 24, 2001, entitled "Nanoscopic Wire-Based Devices and Arrays," by Lieber, et al., published as U.S. Patent Application Publication No. 2002/0130353 on Sep. 19, 2002, now U.S. Pat. No. 6,781,166, issued Aug. 24, 2004; U.S. Provisional Patent Application Ser. No. 60/348,313, filed Nov. 9, 2001, entitled "Transistors, Diodes, Logic Gates and Other Devices Assembled from Nanowire Building Blocks," by Lieber, et al.; U.S. patent application Ser. No. 10/020,004, filed Dec. 11, 2001, entitled "Nanosensors," by Lieber, et al., published as U.S. Patent Application Publication No. 2002/0117659 on Aug. 29, 2002; International Patent Application No. PCT/US01/48230, filed Dec. 11, 2001, entitled "Nanosensors," by Lieber, et al., published as WO 02/48701 on Jun. 20, 2002; U.S. Provisional Patent Application Ser. No. 60/354,642, filed Feb. 6, 2002, entitled "Nanowire Devices Including Emissive Elements and Sensors," by Lieber, et al.; U.S. patent application Ser. No. 10/152,490, filed May 20, 2002, entitled "Nanoscale Wires and Related Devices," by Lieber, et al.; International Patent Application No. PCT/US02/16133, filed May 20, 2002, entitled "Nanoscale Wires and Related Devices," by Lieber, et al., published as WO 03/005450 on Jan. 16, 2003; U.S. patent application Ser. No. 10/196,337, filed Jul. 16, 2002, entitled "Nanoscale Wires and Related Devices," by Lieber, et al., published as U.S. Patent Application Publication No 2003/0089899 on May 15, 2003; U.S. Provisional Patent Application Ser. No. 60/397,121, filed Jul. 19, 2002, entitled "Nanowire Coherent Optical Components," by Lieber, et al.; International Patent Application No. PCT/US03/22061, filed Jul. 16, 2003, entitled "Nanoscale Wires and Related Devices," by Lieber, et al.; U.S. patent application Ser. No. 10/624,135, filed Jul. 21, 2003, entitled "Nanowire Coherent Optical Components," by Lieber, et al.; International Patent Application No. PCT/US03/11078, filed Jul. 21, 2003, entitled "Nanowire Coherent Optical Components," by Lieber, et al., published as WO 2004/010552 on Jan. 29, 2004; U.S. Provisional Patent Application Ser. No. 60/524,301, filed Nov. 20, 2003, entitled "Nanoscale Arrays and Related Devices," by Whang, et al.; U.S. patent application Ser. No. 10/720,020, filed Nov. 21, 2003, entitled "Nanoscale Wires and Related Devices," by Lieber, et al., published as U.S. Patent Application Publication No. 2003/0089899 on May 15, 2003; U.S. patent application Ser. No. 10/734,086, filed Dec. 11, 2003, entitled "Nanowire Coherent Optical Components," by Lieber, et al., published as U.S. Patent Application Publication No. 2004/0213307 on Oct. 28, 2004; U.S. Provisional Patent Application Ser. No. 60/544,800, filed Feb. 13, 2004, entitled "Nanostructures Containing Metal-Semiconductor Compounds," by Lieber, et al.; U.S. Provisional Patent Application Ser. No. 60/551,634, filed Mar. 8, 2004, entitled "Robust Nanostructures," by McAlpine, et al.; U.S. patent application Ser. No. 10/812,653, filed Mar. 29, 2004, entitled "Nanoscopic Wire-Based Devices and Arrays," by Lieber, et al., published as U.S. Patent Application Publication No. 2004/0188721 on Sep. 30, 2004; U.S. Provisional Patent Application Ser. No. 60/579,996, filed Jun. 15, 2004, entitled "Nanosensors," by Wang, et al.; U.S. patent application Ser. No. 10/973,665, filed Oct. 26, 2004, entitled "Nanoscopic Wire-Based Devices and Arrays," by Lieber, et al., published as U.S. Patent Application Publication No. 2005/0117441 on Jun. 2, 2005; U.S. patent application Ser. No. 10/995,075, filed Nov. 22, 2004, entitled "Nanoscale Arrays and Related Devices," by Whang, et al., published as U.S. Patent Application Publication No. 2005/0253137 on Nov. 17, 2005; U.S. Provisional Patent Application Ser. No. 60/633,733, filed Dec. 6, 2004, entitled "Nanoscale Wire Based Data Storage," by Lieber, et al.; U.S. patent application Ser. No. 11/058,443, filed Feb. 14, 2005, entitled "Nanoscale Wires and Related Devices," by Lieber, et al.; International Patent Application No. PCT/US2005/004459, filed Feb. 14, 2005, entitled "Nanostructures Containing Metal-Semiconductor Compounds," by Lieber, et al., published as WO 2005/093831 on Oct. 6, 2005; U.S. patent application Ser. No. 11/137,784, filed May 25, 2005, entitled "Nanoscale Sensors," by Lieber, et al.; U.S. Provisional Patent Application Ser. No. 60/707, 136, filed Aug. 9, 2005, entitled "Nanoscale Sensors," by Lieber, et al.; U.S. Provisional Patent Application Ser. No. 60/790,322, filed Apr. 7, 2006, entitled "Nanoscale Wire Methods and Devices," by Lieber, et al.; and U.S. Provisional Patent Application Ser. No. 60/812,884, filed Jun. 12, 2006, entitled "Nanosensors and Related Technologies," by Lieber, et al.

The following examples are intended to illustrate certain embodiments of the present invention, but do not exemplify the full scope of the invention.

EXAMPLE 1

In this example, a nanowire field effect transistor was prepared, on which a PNA sequence was immobilized onto a portion of the nanowire for single DNA molecule detection.

Figure 2A:
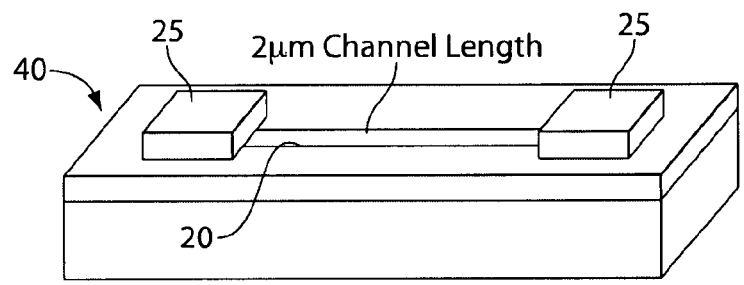
Figure 2B:
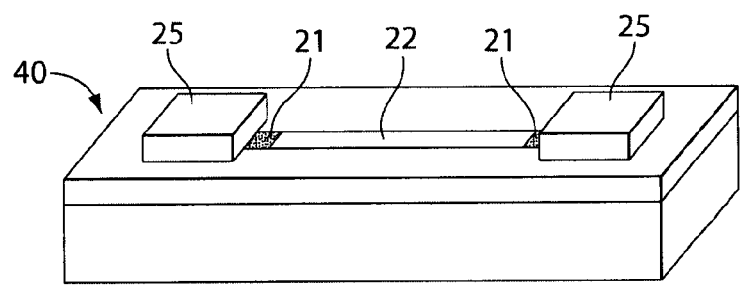
Figure 2C:
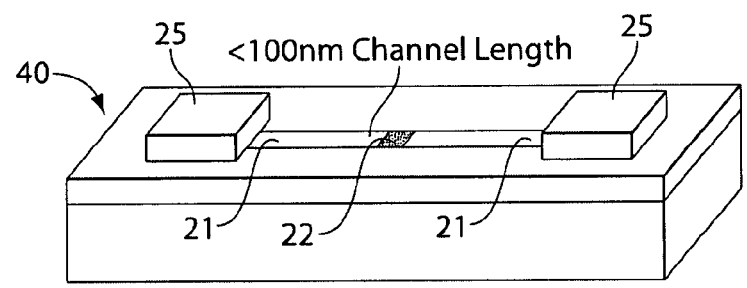
Figure 2D:
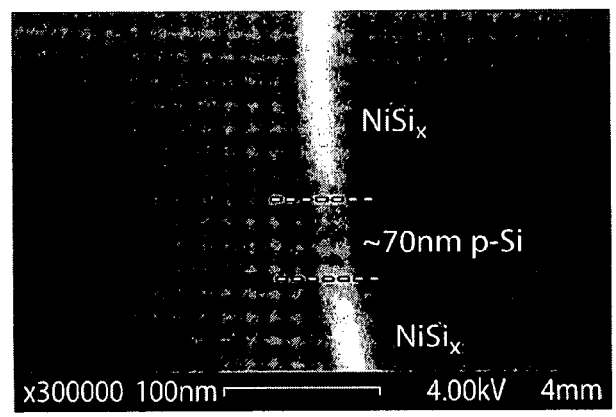

In FIG. 2A, silicon nanowire 20 was synthesized by chemical vapor deposition using 10 nm gold nanoparticles as the catalyst particles, silane as reactant, and diborane as a p-type dopant, with a Si:B ratio of 4000:1. A device 40 comprising a silicon nanowire field effect transistor (FET) was fabricated using photolithography, with a defined channel length of about 2 micrometers and 50 nm of nickel evaporated on each end of nanowire 20 to make contacts 25. After lift-off, device 40 was pre-annealed at 380° C. in $H_2/N_2$ forming gas for 90 seconds. Then device 40 was annealed again at 415° C. to facilitate diffusion of nickel and formation of nickel silicide along the silicon nanowire (i.e., to define a first portion of the nanowire 21) (FIG. 2B). For a 10 nm diameter silicon nanowire, 40 seconds of annealing at 415° C. resulted in a channel length (i.e., a second portion of the nanowire 22) of less than about 100 nm (FIG. 2C), as shown in the SEM image of a specific device with a ~70 nm channel (FIG. 2D).

Figure 2E:
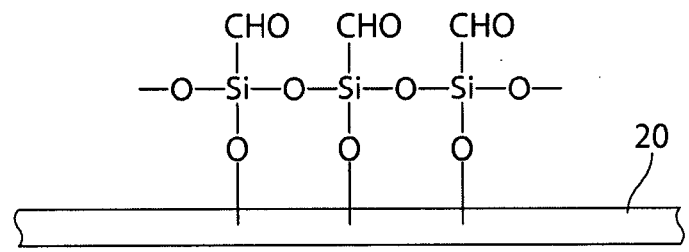
Figure 2F:
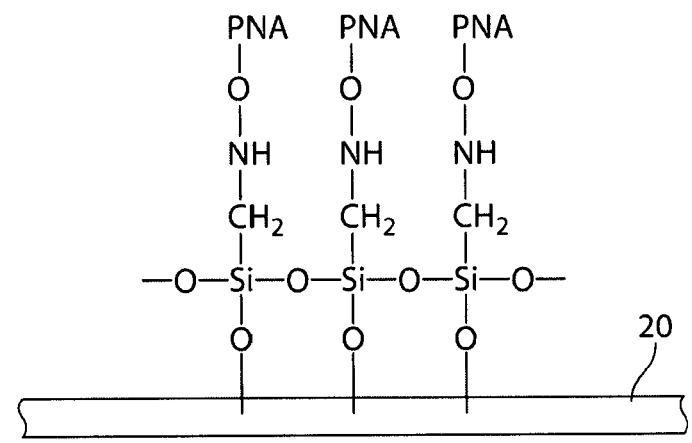

Next, the device 40 was exposed to aldehyde propyltrimethoxysilane or 3-mercaptopropyltrimethoxysilane (2% silane in ethanol) for 60 minutes (FIG. 2E and FIG. 2J). The silane reacted with the silicon oxide surface on the second portions of the nanowire 22 and can generally give a monolayer of the function group within 60 minutes. After exposure to the silane and rinse with ethanol thoroughly, the device 40 was baked at 120° C. in $N_2$ for 10 minutes. Then, device 40 was incubated with 20 microliters of a 30 micromolar Lys-O-PNA sequence (for the aldehyde silane surface), with 4 mM $NaBH_3CN$ in 10 mM phosphate buffer at a pH of 8.3 overnight, or a MCC-OO-PNA sequence (i.e., a maleimide-linker-PNA moiety for the thiol silane surface) in 10 mM phosphate buffer at a pH 7 for 4 hours, resulting in immobilization of the PNA sequence relative to the second portion of the nanowire 22 (FIG. 2F). The unreacted aldehyde groups were blocked by incubation with ethanolamine in the presence of 4 mM $NaBH_3CN$ in 10 mM phosphate buffer. The PNA sequence used in this example was ATCATCTTTG (SEQ ID NO: 1), but other PNA sequences can be used as well. Additionally, other surface chemistry can also be used to immobilize the PNA sequence, for example, as is shown in FIGS. 2D-2F, e.g., involving epoxide ring opening reactions (FIG. 2I).

Figure 2G:
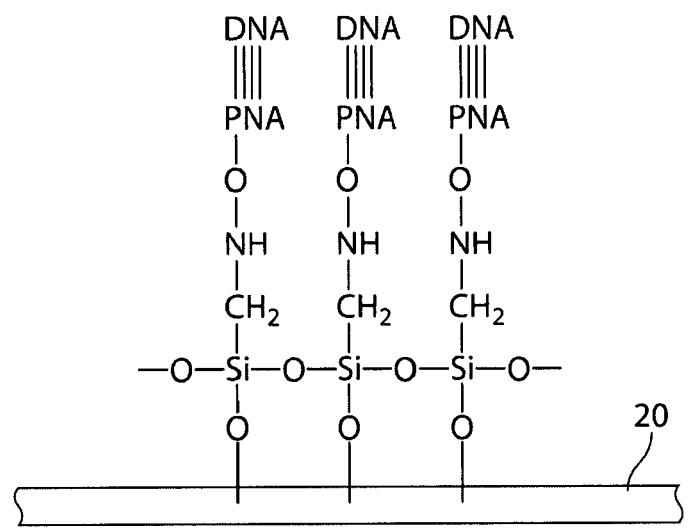
Figure 2K:
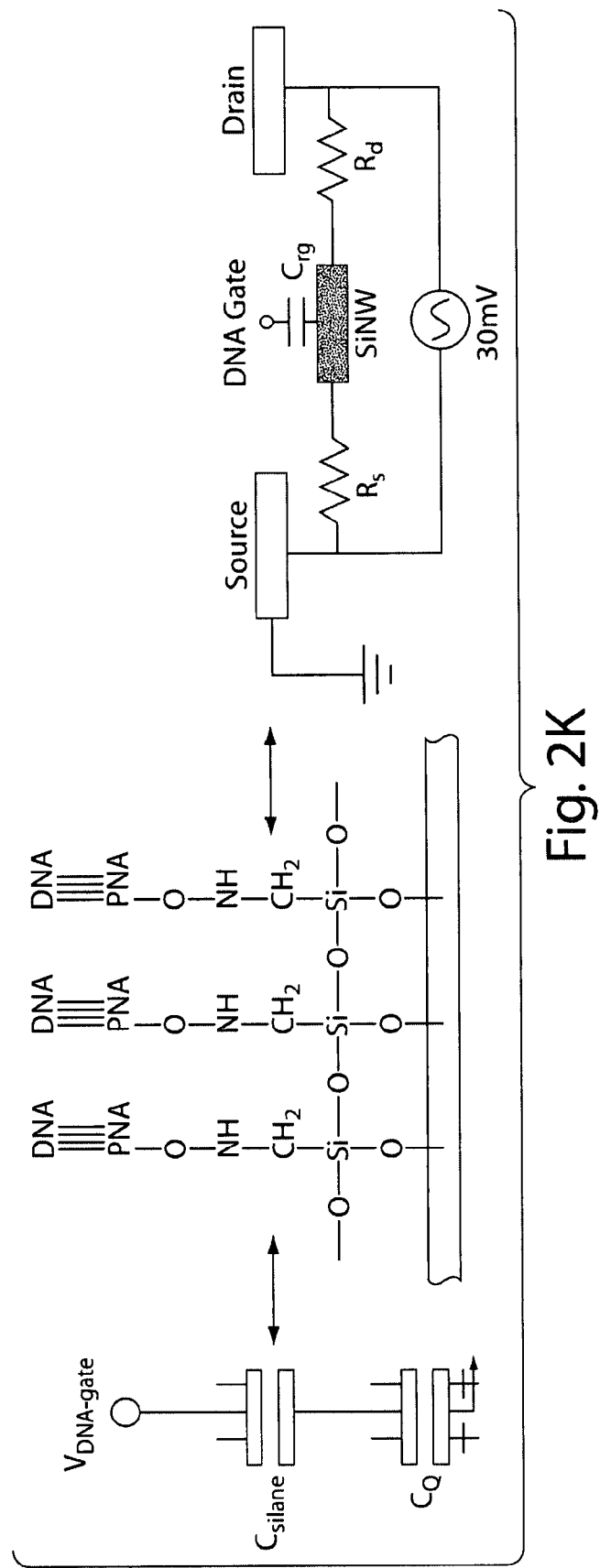

Device 40 could then be used as a sensor, e.g., if the nanowire FET is gated by charged molecules. For instance, as discussed in the below examples, by exposing the PNA sequence to a substantially complementary DNA sequence (e.g., 1 nanomolar DNA in 10 micromolar PBS), association of the DNA sequence to the PNA sequence may be determined (FIG. 2G). (See FIG. 2K, illustrating the electronic circuit of the FET.)

EXAMPLE 2

In this example, the nanoscale sensor device fabricated in Example 1 (having the PNA binding partner described in that example) was used to determine DNA analytes in a solution. The PNA sequence was ATCATCTTTG (SEQ ID NO: 1) with the N-terminus attached to the nanowire surface. The buffer solutions used in all measurements was 10 micromolar PBS. The DNA sequences were dissolved in the same buffer solution. Two DNA sequences used in this example were TTTTTTTTTT (SEQ ID NO: 6) ("poly(T)$_{10}$") and ATCAAAGATG (SEQ ID NO: 5). The DNA sequence ATCAAAGATG (SEQ ID NO: 5) was expected to hybridize with the PNA through the IS interaction of 8 base pairs, i.e. the CAAAGATG (SEQ ID NO: 7) of the DNA to the CATCTTTG (SEQ ID NO: 8) sequence of the PNA. The AC amplitude through the nanowire in this example was 30 mV and the frequency was 17 Hz.

Figure 3A:
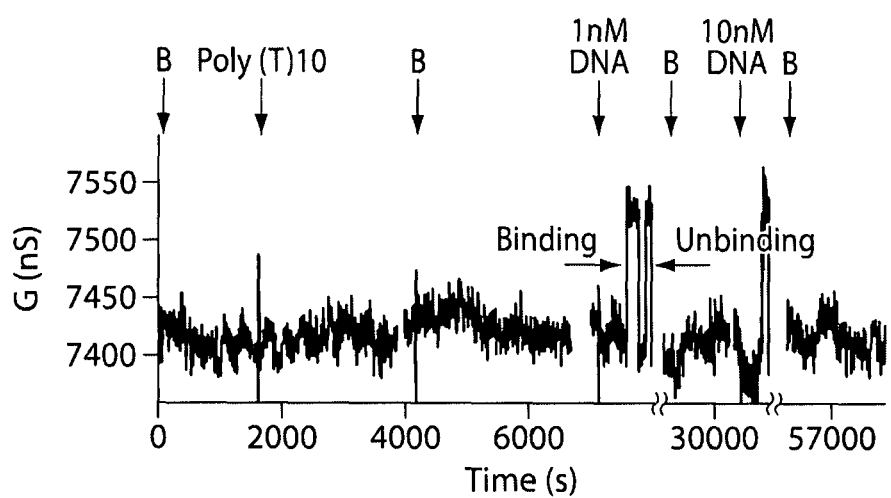
FIGS. 3A-3G illustrate the determination of the association/dissociation of nucleic acid molecules to binding partners at different concentrations, according to one embodiment of the invention.

FIG. 3A illustrates the conductance (in nanosiemens) vs. time (in seconds) data recorded for the PNA-modified p-type silicon nanowire after sequentially delivery of the following solutions: buffer, 1 nM poly(T)$_{10}$, buffer, 1 nM ATCAAA-GATG (SEQ ID NO: 5), buffer, 10 nM ATCAAAGATG (SEQ ID NO: 5), and buffer. No measurable conductance signal was observed in both the buffer and 1 nM poly(T)$_{10}$ solutions. However, upon flowing matched DNA sequence ATCAAA-GATG (SEQ ID NO: 5), one DNA molecule appeared to hybridize with one PNA molecule on the nanowire, as shown in FIG. 3A. It is believed that the negative charges on the DNA molecule produces positive image charges in the nanowire, so the conductance of the p-type nanowire jumped to a higher value, which was determined in real time and indicated by the arrows in FIG. 3A. When the DNA dehybridizes and leaves the nanowire surface, the conductance of the nanowire jumped back to the original value. This behavior (repeated binding/unbinding of DNA) continued while the DNA solution was passed over the nanowires used in this example.

Figure 3B:
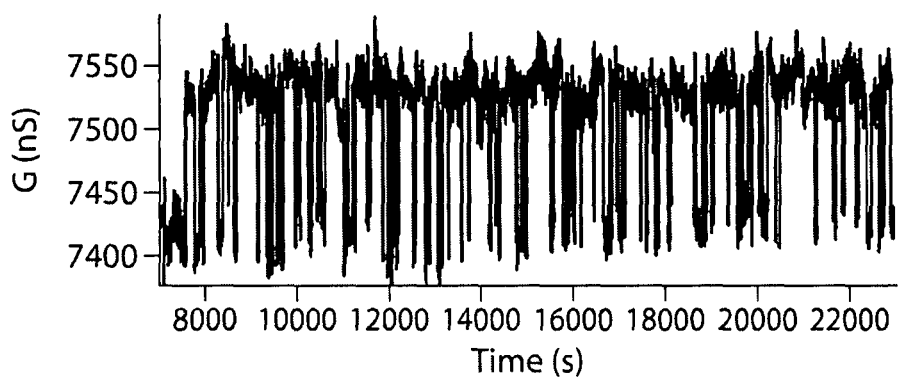
Figure 3C:
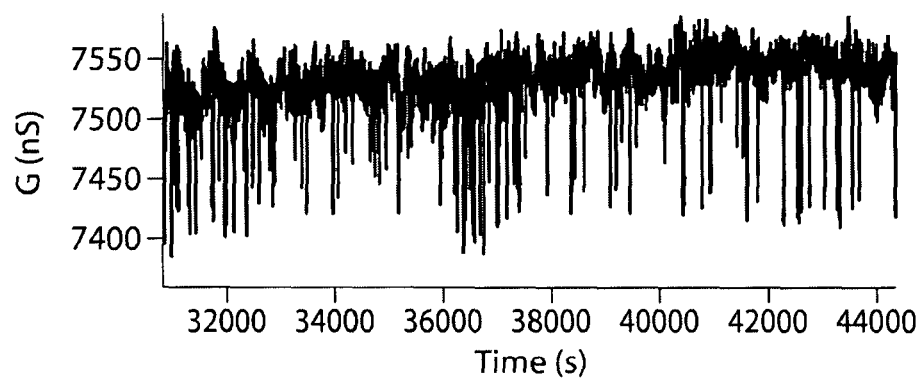
Figure 3D:
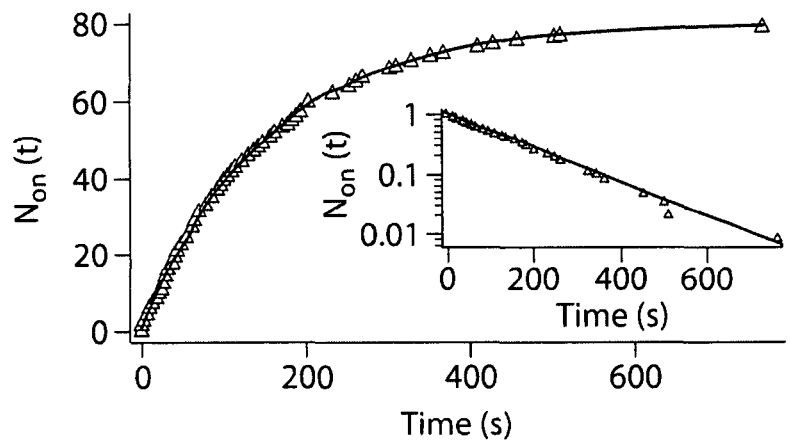
Figure 3E:
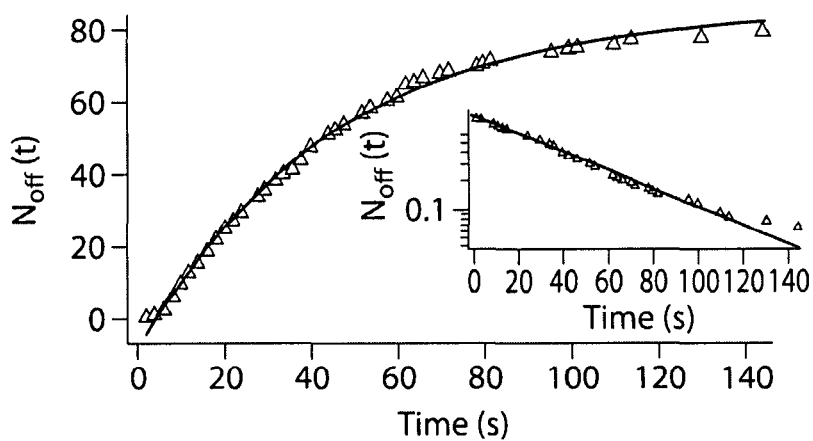
Figure 3F:
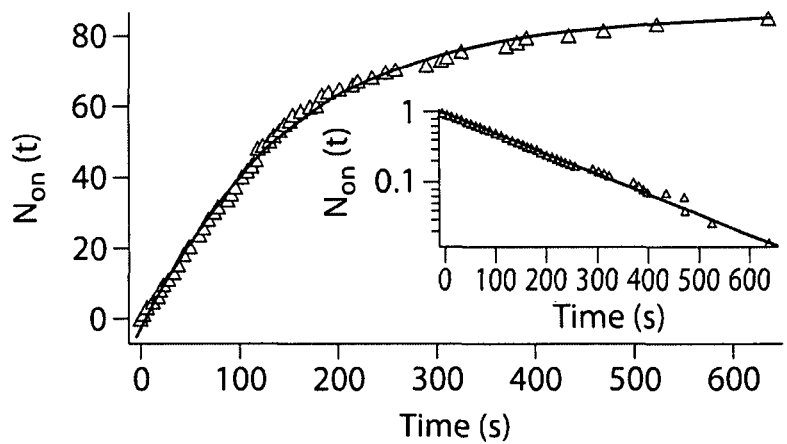
Figure 3G:
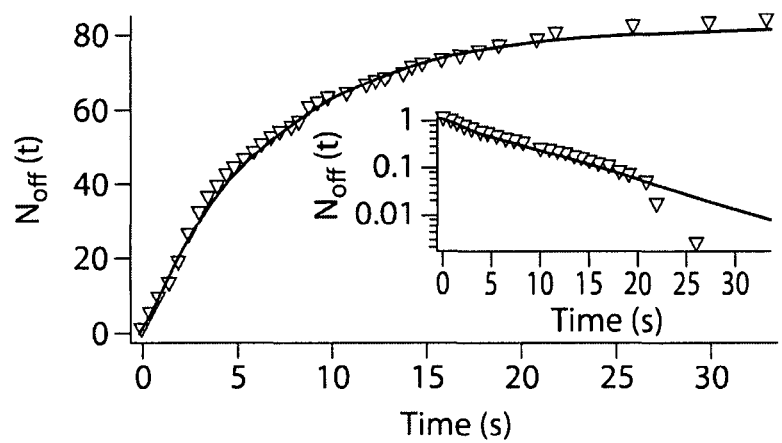

FIG. 3B and FIG. 3C illustrate detailed time trajectories for the 1 nM and 10 nM DNA solutions. From each of these time trajectories, the dwell times with DNA on and off the PNA probe could be determined, which could be used to determine unbinding and binding rate of the DNA molecules to the PNA probes on the nanowire surface, as shown in FIG. 3D-3G. In these figures, $N_{on}(t)$ or $N_{off}(t)$ represents the number of events with dwell times of the "on" or "off" state shorter than time t, which could then be used to determine the unbinding or binding rate constants (i.e., dissociation/association rate constants). The grey lines in these figures are the single-exponential fit of the processes, which gave $k_{off}$(1 nM)=0.0065 s$^{-1}$ (FIG. 3D), $k_{on}$(1 nM)=0.022 s$^{-1}$ (FIG. 3E), $k_{off}$(10 nM)=0.0068 s$^{-1}$ (FIG. 3F), and $k_{on}$(10 nM)=0.14 s$^{-1}$ (FIG. 3G) respectively. It was found in this example that the unbinding rate constants were similar for 1 nM and 10 nM DNA solutions, i.e., 0.0065 s$^{-1}$ and 0.0068 s$^{-1}$, respectively. However for the binding process, the rate constant for the 10 nM DNA solution was about 6.4 times greater than for the 1 nM DNA solution.

This example demonstrates the ability to detect specifically the single molecule binding and unbinding events onto a silicon nanowire surface, and to measure the concentration dependent binding and unbinding rate constants of the hybridization between DNA and PNA e.g., to determine the concentration of the DNA in the solution.

EXAMPLE 3

In this example, the nanoscale sensor fabricated in Example 1 (having the PNA binding partner described in that example) was used to discriminate mismatched DNA and perfectly matched DNA sequences at the single molecule level. In this example, three types of DNA were used: perfectly complementary DNA, having a sequence CAAAGAT-GAT (SEQ ID NO: 2), or substantially complementary DNA that was not perfectly complementary, but having 1 or 2 mismatches, CAAACATGAT (SEQ ID NO: 3) or CAAAC-CTGAT (SEQ ID NO: 4), respectively. The DNA were all at concentration of 100 nM. The AC amplitude through the nanowires in this example was 20 mV and the frequency was 509 Hz.

Figure 4A:
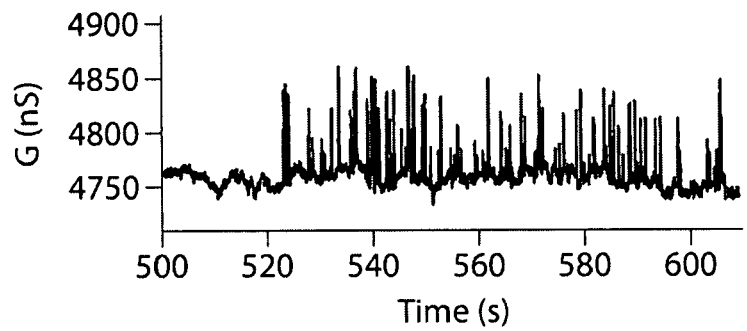
FIGS. 4A-4G illustrate the determination of kinetics of association and dissociation of an analyte with a binding partner, in one embodiment of the invention.
Figure 4B:
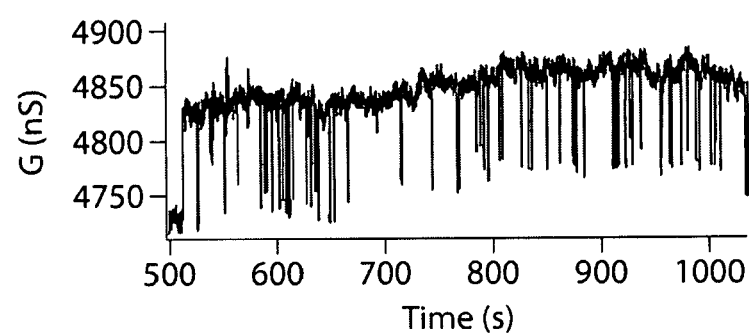
Figure 4C:
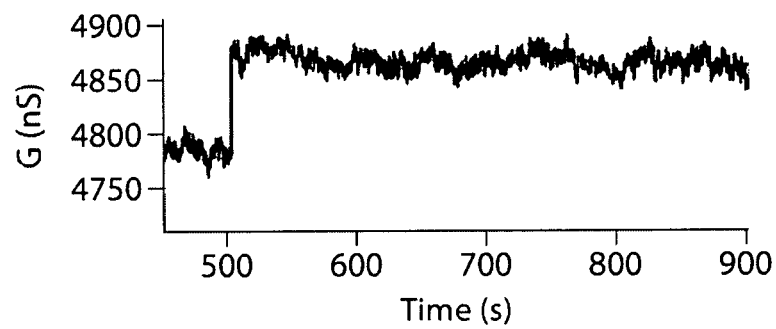
Figure 4D:
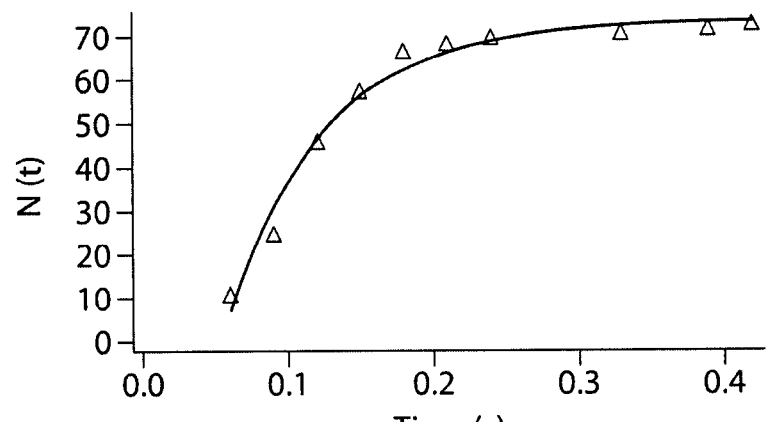
Figure 4E:
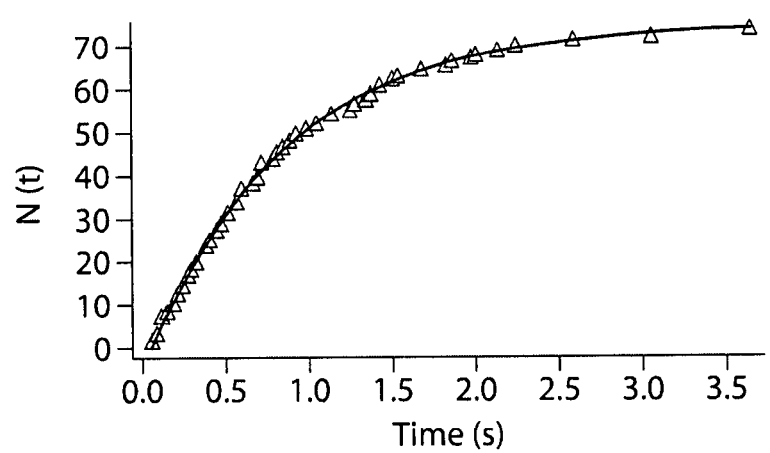
Figure 4F:
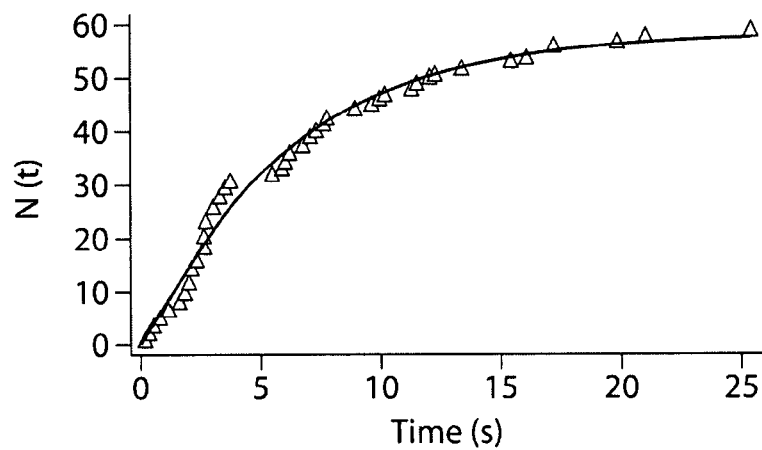
Figure 4G:
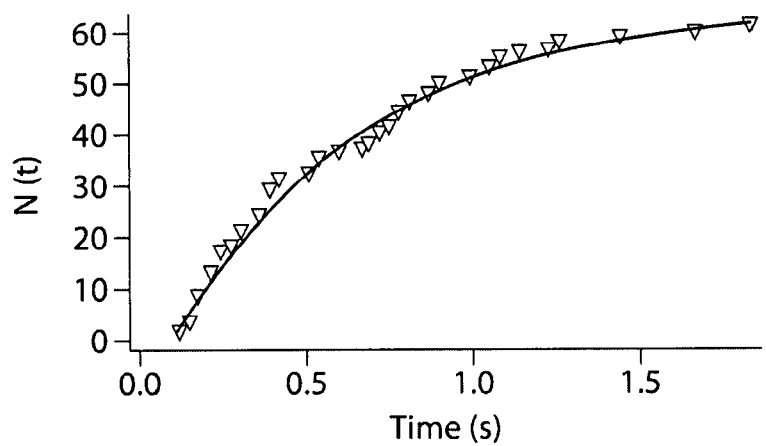

FIGS. 4A-4C are plots of conductance (in nS) with respect to time (in s) for solutions containing DNA with a single mismatch in the middle, DNA with two mismatches in the middle, and perfectly complementary DNA. By measuring the dwell times of the "on" and "off" states as in Example 2, the rate constants of binding and unbinding (i.e., association/dissociation) were determined for a single mismatched DNA and double mismatched DNA. (FIGS. 4C and 4D for $k_{off}$ and $k_{on}$ for FIG. 4A, respectively, and FIGS. 4E and 4F for $k_{off}$ and $k_{on}$ for FIG. 4B, respectively). Note that FIGS. 4A-4C only show the portions of the experiments where the nanowires were exposed to DNA. Curve-fitting of these data yielded, for a single mismatch, $k_{on}$=1.67 s$^{-1}$ and $k_{off}$=0.166 s$^{-1}$, and for a double mismatch, $k_{on}$=1.20 s$^{-1}$ and $k_{off}$=14.80 s$^{-1}$. Thus, while the binding rate constants were comparable for single and double mismatched sequences, the unbinding rate constants were markedly different, indicating that the double mismatch was approximately 90 times more easily to leave than the single mismatch. Further, no dissociation appeared to have occurred between the perfectly complementary DNA and its PNA binding partner during the experiment (>2000 s).

This example thus demonstrates the ability to both discriminate single-point mutation in DNA sequences and reveal the underlying biophysical relevance of binding and unbinding steps.

EXAMPLE 4

This example illustrates that, according to certain embodiments of the invention, a nanowire may be used to detect multiple binding or association of individual DNA molecules.

Figure 5:
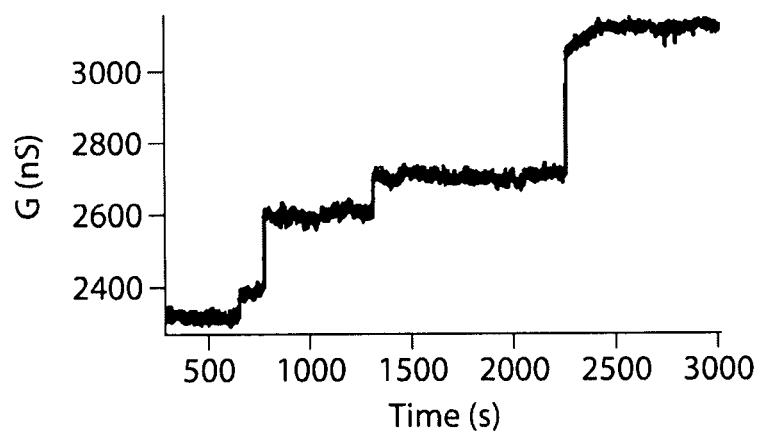
FIG. 5 illustrates the determination of multiple associations of individual nucleic acid molecules to binding partners, according to some embodiments of the invention.

A nanowire was prepared using techniques similar to those described in Example 1, on which a portion of the nanowire a PNA sequence was immobilized. The PNA sequence was ATCATCTTTG (SEQ ID NO: 1). The PNA was exposed to DNA having a sequence CAAAGATGAT (SEQ ID NO: 2), i.e., perfectly complementary DNA. The conductance vs. time data is shown in FIG. 5. In this figure, the conductance increases by discrete "steps," which each correspond to individual binding events between one DNA molecule and one PNA molecule on the nanowire surface. It should be noted that no unbinding was detected between the PNA and the perfectly complementary DNA.

EXAMPLE 5

In this example, with reference to FIG. 7, the sensitivity of nanoscale wires used in certain embodiments of the invention are illustrated. However, this theoretical discussion is presented by way of illustration only, and should not be construed as being limiting in any way.

FIG. 7 shows a nanoscale wire, used in a FET, having a contact resistances $R_s$ (source) and $R_d$ (drain). $R_c$, the total contact resistance, is:

$$R_c = R_s + R_d.$$

Within the wire itself, $R_1$ and $R_2$ are the resistances of the portions of the nanoscale wire (portions having lengths $l_1$ and $l_2$, respectively) that are not "gated" or altered upon binding of the analyte to the nanoscale wire (e.g., to a binding partner immobilized relative to the nanoscale wire). Under the diffusion limit (e.g., in a silicon nanowire):

$$R_1 + R_2 = r(l_1 + l_2),$$

where r is the resistivity per unit length of the nanoscale wire.

$R_g$ can be defined as the resistance of the portion of the nanoscale wire that is gated (altered) upon binding of one analyte molecule. Defining $R_g^0$ as the resistance, before binding, and $R_g^1$ as the resistance after binding, then the difference is:

$$R_g^1 = R_g^0 - \Delta R_g,$$

where $\Delta R_g$ is the resistance change. The resistance change may be determined, e.g., by the charge and/or size of the analyte (e.g., of DNA), electronic properties of the nanoscale wire, and/or the distance between the analyte and the nanoscale wire. In the treatment in this example, this value can be treated as a constant for a given analyte, nanoscale wire, and surface chemistry of the device.

This yields a conductance change, $\Delta G$, of:

$$\Delta G = \frac{1}{R_c + r(l_1 + l_2) + R_g^0 - \Delta R_g} - \frac{1}{R_c + r(l_1 + l_2) + R_g^0}$$

$$= \frac{\Delta R_g}{[R_c + r(l_1 + l_2) + R_g^0 - \Delta R_g][R_c + r(l_1 + l_2) + R_g^0]}.$$

Thus, as $R_c$ decreases, the conductance change signal increases, and as the length ($l_1 + l_2$) decreases, the conductance change signal increases. Also, good electronic properties of the nanowire, e.g. high mobility, and good surface chemistry can give a relatively high $\Delta R_g$ and a relatively high $\Delta G$. Thus, better contacts, shorter lengths, and/or good nanomaterial and surface chemistries may yield higher sensitivities, i.e., $\Delta G$.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion to of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B")

can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
a nanoscale wire comprising a first portion and a second portion laterally defined along the length of the nanoscale wire, the first portion consisting essentially of a single crystal of a transition metal silicide compound, the compound being stoichiometric, and the second portion comprising a semiconductor, having a length of less than 100 nm, and having immobilized relative thereto a binding partner of an analyte, wherein the first portion is free of the binding partner.

2. The article of claim 1, wherein the transition metal comprises nickel.

3. The article of claim 1, wherein the nanoscale wire is part of a FET.

4. The article of claim 1, wherein the nanoscale wire further comprises a third portion being defined laterally along the nanowire, the second portion separating the first portion and the third portion, the third portion consisting essentially of a single crystal of the transition metal-semiconductor compound.

5. The article of claim 1, wherein the second portion has a length of less than 50 nm.

6. The article of claim 1, wherein the second portion has a length of less than 30 nm.

7. The article of claim 1, wherein the second portion further comprises a binding partner to an analyte immobilized relative thereto.

8. The article of claim 7, wherein the analyte is a nucleic acid.

9. The article of claim 7, wherein the binding partner is a nucleic acid.

10. The article of claim 7, wherein the article comprises a plurality of nanoscale wires, each comprising distinguishable nucleic acids immobilized relative thereto.

11. An article, comprising:
a sample exposure region able to hold a solution containing an analyte;
a nanoscale wire positioned at least partially adjacent to or within the sample exposure region, the nanoscale wire comprising a first portion and a second portion, each laterally defined along the nanoscale wire, the second portion comprising a semiconductor and having immobilized relative thereto a binding partner able to bind to the analyte contained in the solution, and the first portion being free of the binding partner and comprising a conductive transition metal silicide compound, the compound being stoichiometric,
wherein the binding partner is able to bind one or more molecules of the analyte, wherein the analyte, when bound to the binding partner, has a Debye screening length within the solution that is greater than the greatest dimension of the second portion of the nanoscale wire.

12. The article of claim 11, wherein the analyte comprises a nucleic acid.

13. The article of claim 11, wherein a single molecule of the analyte, when bound to the binding partner, has a Debye screening length than the greatest dimension of the second portion of the nanoscale wire.

14. The article of claim 11, wherein the transition metal silicide compound consists essentially of a single crystal.

15. The article of claim 11, wherein the nanoscale wire comprises the first portion, the second portion, and a third portion each laterally defined along the nanoscale wire, wherein the third portion is free of the binding partner and comprises a conductive transition metal-semiconductor compound.

* * * * *